US010568892B2

(12) United States Patent
Zhang et al.

(10) Patent No.: US 10,568,892 B2
(45) Date of Patent: Feb. 25, 2020

(54) CYCLOARTANE TETRACYCLIC TRITERPENOID COMPOUND, PREPARATION METHOD THEREFOR AND USE THEREOF

(71) Applicants: Hefei Cosource Pharmaceuticals Inc., Hefei (CN); Hefei Blooming Drug Safety Evaluation Co., Ltd., Heifei (CN)

(72) Inventors: Shanchun Zhang, Hefei (CN); Shu Gao, Hefei (CN); Xiaorong Lu, Hefei (CN); Hongzhang Sun, Hefei (CN); Yijun Bao, Hefei (CN); Bin Yang, Hefei (CN); Jiashi Peng, Hefei (CN)

(73) Assignees: Hefei Cosource Pharmaceuticals Inc., Hefei, Anhui Province (CN); Hefei Blooming Drug Safety Evaluation Co., Ltd., Hefei, Anhui Province (CN)

( * ) Notice: Subject to any disclaimer, the term of this patent is extended or adjusted under 35 U.S.C. 154(b) by 0 days.

(21) Appl. No.: 16/083,390

(22) PCT Filed: Feb. 3, 2017

(86) PCT No.: PCT/CN2017/072816
§ 371 (c)(1),
(2) Date: Sep. 7, 2018

(87) PCT Pub. No.: WO2018/076568
PCT Pub. Date: May 30, 2018

(65) Prior Publication Data
US 2019/0240238 A1 Aug. 8, 2019

(30) Foreign Application Priority Data
Oct. 25, 2016 (CN) .......................... 2016 1 0936156

(51) Int. Cl.
A61K 31/57 (2006.01)
A61P 9/00 (2006.01)
A61P 9/06 (2006.01)
A61P 9/10 (2006.01)
A61P 9/04 (2006.01)
A61K 31/56 (2006.01)

(52) U.S. Cl.
CPC .............. A61K 31/57 (2013.01); A61K 31/56 (2013.01); A61P 9/00 (2018.01); A61P 9/04 (2018.01); A61P 9/06 (2018.01); A61P 9/10 (2018.01)

(58) Field of Classification Search
CPC . A61K 31/56; A61K 31/57; A61P 9/00; A61P 9/04; A61P 9/06; A61P 9/10
See application file for complete search history.

(56) References Cited

FOREIGN PATENT DOCUMENTS

CN          1345727 A    *    4/2002

OTHER PUBLICATIONS

Rahman (J. Nat. Prod. 1997, 60, 770-774).*
Kupchan et al. (J. Org. Chem. (1966), Issue 2 (31), p. 608-610).*
Khong-Huu-Laine et al. (Bulletin de la Societe Chimique de France (1966), Issue 4, pp. 1216-1221).*
ISA/CN, International Search Report and Written Opinion for PCT/CN2017/072816 (dated Jul. 28, 2017).

* cited by examiner

Primary Examiner — Valerie Rodriguez-Garcia
(74) Attorney, Agent, or Firm — Fish & Richardson P.C.

(57) ABSTRACT

The present invention relates to the field of natural medicine and pharmaceutical chemistry, and in particular relates to a cycloartane tetracyclic triterpenoid compound (I), a preparation method thereof and the medical use thereof. The pharmacodynamic tests demonstrate that the compound of the present invention has a pharmacodynamic activity on heart and cerebral vessels and can be used to prevent or treat cardiovascular and/or cerebrovascular diseases such as arrhythmia, myocardial infarction, and coronary heart disease or the like.

13 Claims, 2 Drawing Sheets

CYCLOARTANE TETRACYCLIC TRITERPENOID COMPOUND, PREPARATION METHOD THEREFOR AND USE THEREOF

CROSS-REFERENCE TO RELATED APPLICATIONS

This application is a U.S. National Phase application under 35 U.S.C. § 371 of International Patent Application No. PCT/CN2017/072816, filed Feb. 3, 2017, which claims priority to Chinese Application No. 201610936156.X, filed on Oct. 25, 2016. The entire contents of the parent applications are hereby incorporated by reference.

TECHNICAL FIELD

The present invention relates to the field of natural medicine and pharmaceutical chemistry, and in particular relates to a cycloartane tetracyclic triterpenoid compound, a preparation method thereof and the medical use thereof.

BACKGROUND

Cycloartane triterpenoids are widely existed in the plants, in which C-9 and C-19 form a three-membered ring to form a special type of tetracyclic triterpenoid. These compounds have complex structures and diverse biological activities. The literature reports that they have anti-tumor activities, anti-viral activities, antibacterial and anti-inflammatory activities, immunomodulatory activities, cardiovascular effects, and protective effects on liver damage (TIAN Ze et al., Review of Bioactivities of Natural Cycloartane Triterpenoids, *China Journal of Chinese Materia*, 2006, 31(8): 626-629). The natural products of typical cycloartane triterpenoids are: for example, Cycloastragenol (derived from *Radix Astragali*), Astragaloside (derived from *Radix Astragali*), Cimigenol (derived from *rhizoma cimicifugae*), Oryzanol (derived from rice bran oil), Huangyangning (Cyclovirobuxin A-D, derived from *Buxus sempervirens*), and Cyclobuxine D, whose structures are shown as follows:

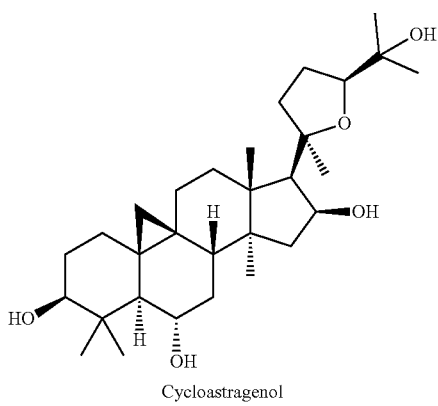
Cycloastragenol

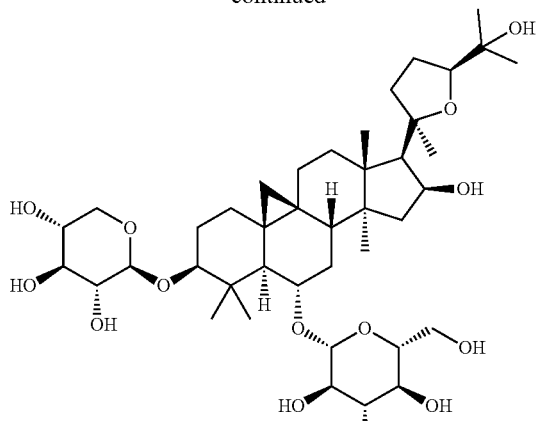
Astragaloside

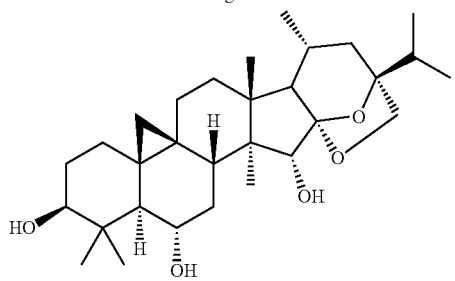
Cimigenol

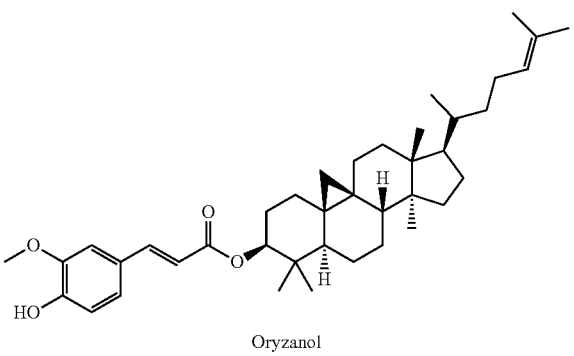
Oryzanol

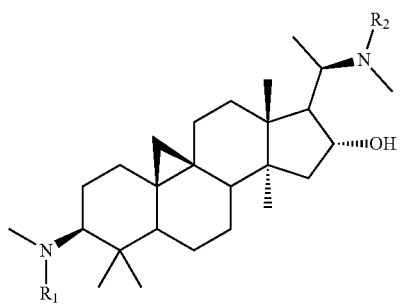

$R_1 = CH_3$, $R_2 = CH_3$   A
$R_1 = CH_3$, $R_2 = H$      B
$R_1 = H$,   $R_2 = CH_3$    C
$R_1 = H$,   $R_2 = H$       D

Cyclovirobuxin A ~ D

-continued

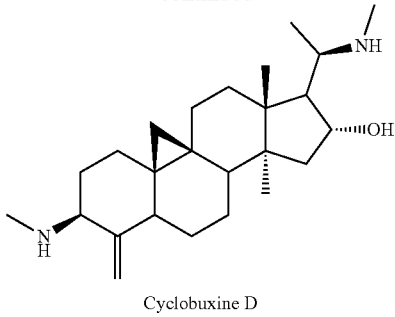

Cyclobuxine D

Among them, the research on astragaloside as a representative drug is a particular hotspot, and the development of its injection for angina pectoris is in the clinical trial stage. The Huangyangning tablet as Chinese patent medicine is included in Chinese Pharmacopoeia for the treatment of thoracic obstruction and cardiodynia, knotted pulse, coronary heart disease, and arrhythmia caused by stagnation of blood stasis. Oryzanol injection is used for autonomic nerve dysfunction, premenstrual tension syndrome, menopausal syndrome, and primary dysmenorrhea.

The structural modifications on steroidal drugs with tetracyclic triterpenoid structure characteristics exist throughout the history of drug development, in which the structural modifications and developments of glucocorticoid anti-inflammatory drugs are the most well-known. From prednisone to hydrocortisone, prednisolone, dexamethasone, and various water-soluble and fat-soluble prodrugs, every tiny structural change has brought about a significant increase in clinical application value. There have been increasing attentions paid to the research on cycloartane natural products also as tetracyclic triterpenoids to increase the clinical application value by improving pharmacokinetic characteristics, enhancing the pharmacological efficacy, and reducing toxic and side effects through structural modifications.

Cardiovascular and/or cerebrovascular diseases, a type of common disease that threatens humans especially middle-aged and old people who are over 50 years old, are characterized in high prevalence, high disability, and high mortality. Even if the most advanced and perfect treatment at present is applied, more than 50% of the survivors of cardiovascular and/or cerebrovascular accidents cannot completely take care of themselves. The number of people who die of cardiovascular and/or cerebrovascular diseases every year in the world is as high as 15 millions, ranking the first in all causes of death. The China National Cardiovascular Disease Center recently published the "China Cardiovascular Disease Report 2015." This report shows that 2 out of every 5 deaths in China died of cardiovascular disease. Cardiovascular mortality is still the leading cause in death from disease, higher than cancer and other diseases. According to the report, in 2014, the mortality of cardiovascular disease in urban areas of China was 261.99/100,000 persons, wherein the mortality of heart disease was 136.21/100,000 persons, and the mortality of cerebrovascular disease was 125.78/100,000 persons (52.25/10,000 persons for cerebral hemorrhage, and 41.99/100,000 persons for cerebral infarction).

Therefore, it is quite necessary to develop a drug for the remarkable prevention and treatment of cardiovascular and/or cerebrovascular diseases. Said drug should have good drug absorption characteristics, facilitate long-term oral administration or first-aid administration, and especially have excellent pharmacological activities for prevention or treatment as well as favorable safety and therapeutic window.

SUMMARY

The present invention discloses cycloartane tetracyclic triterpenoids having a desired pharmacodynamic activity on heart and/or cerebral vessels and used to prevent or treat cardiovascular and/or cerebrovascular diseases such as arrhythmia, myocardial infarction, and coronary heart disease or the like, whose structural formula is as shown in formula (I):

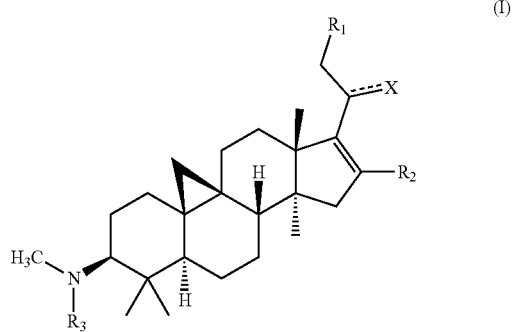

wherein,
═X represents —OH, ═O, ═NOR$_a$, or ═NOCOR$_b$, wherein R$_a$ represents hydrogen, methyl, ethyl, propyl, isopropyl, or butyl; R$_b$ represents C$_1$-C$_{10}$ alkyl, C$_2$-C$_{10}$ alkenyl, or C$_6$-C$_{12}$ aryl optionally having a substituent, wherein the substituent is selected from halogen, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group;

R$_1$ represents hydrogen, hydroxy, ORE, or OCOR$_d$, wherein R$_c$ represents methyl, ethyl, propyl, isopropyl, butyl, pentyl, cyclopropyl, cyclobutyl, cyclopentyl, or cyclohexyl; R$_d$ represents C$_1$-C$_{10}$ alkyl, C$_3$-C$_{10}$ cycloalkyl, C$_2$-C$_{10}$ alkenyl, C$_6$-C$_{12}$ aryl, or heteroaryl optionally having a substituent, the heteroaryl being a monocyclic or fused ring having 5 to 12 ring atoms and containing 1 to 4 ring heteroatoms selected from N, O, or S, the remaining ring atoms being C; wherein the substituent is selected from halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group;

R$_2$ is selected from hydrogen, halogen, methyl, ethyl, propyl, isopropyl, butyl, pentyl, cyclopropyl, cyclobutyl, cyclopentyl, or cyclohexyl; and R$_3$ is selected from hydrogen, methyl, ethyl, propyl, isopropyl, butyl, pentyl, cyclopropyl, cyclobutyl, cyclopentyl, or cyclohexyl.

The present invention excludes the compounds wherein ═X, represents ═O, both R$_1$ and R$_2$ represent H, and R$_3$ represents CH$_3$.

Preferably, ═X represents ═O or ═NOH; more preferably, ═X represents ═O.

Preferably, R$_1$ represents hydrogen, hydroxy, or OCOR$_d$, wherein R$_d$ is C$_1$-C$_{10}$ alkyl, C$_3$-C$_{10}$ cycloalkyl, C$_2$-C$_{10}$ alkenyl, or C$_6$-C$_{12}$ aryl optionally having a substituent; wherein the substituent is selected from halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group.

More preferably, wherein $R_d$ is $C_1$-$C_{10}$ alkyl, vinyl, or phenyl optionally having a substituent, wherein the substituent is halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group.

Preferably, $R_1$ further represents:

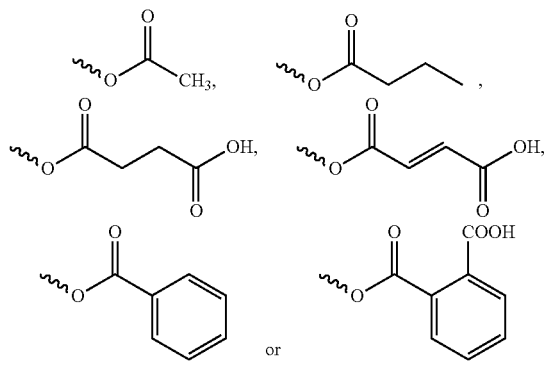

or

Preferably, $R_2$ represents hydrogen, fluorine, or methyl.
Preferably, $R_3$ represents hydrogen, methyl, ethyl, propyl, isopropyl, or cyclopropyl.

DESCRIPTION OF EMBODIMENTS

Figure 1:
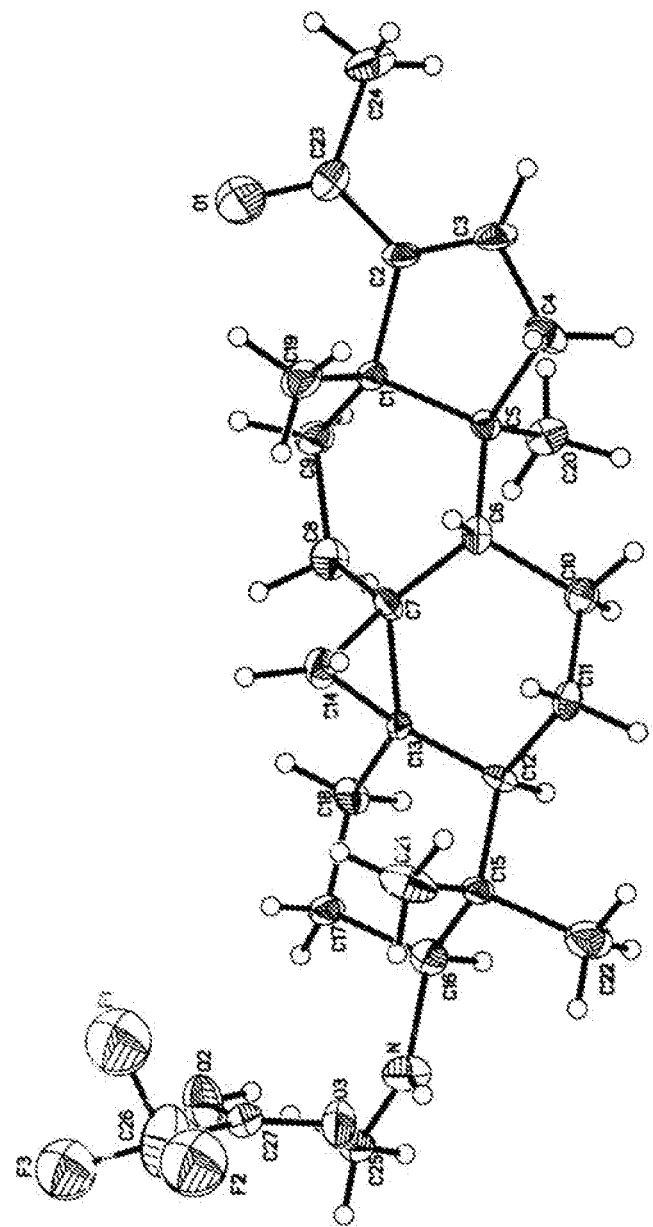
FIG. 1 is an X ray-single crystal diffraction spectrum of a trifluoroacetate of the compound in Example 1.
Figure 2A:
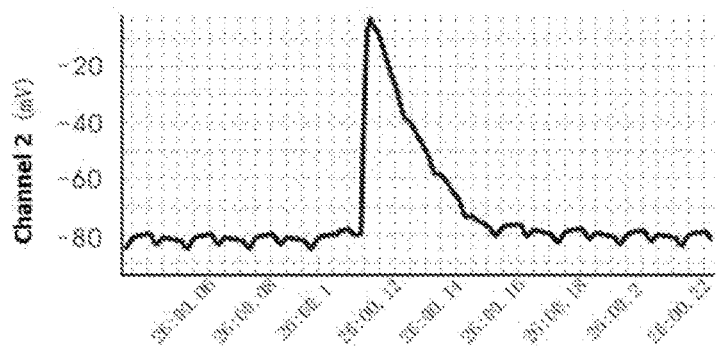
FIG. 2 is an action potential diagram of the ventricular mastoid muscle of guinea pig as recorded by an electrophysiology device (2a: pre-administration of 10 μM amiodarone; 2b: post-administration of 10 μM amiodarone; 2c: pre-administration of 0.05 μM Compound 369 of Example 1; 2d: post-administration of 0.05 μM Compound 369 of Example 1).
Figure 2B:
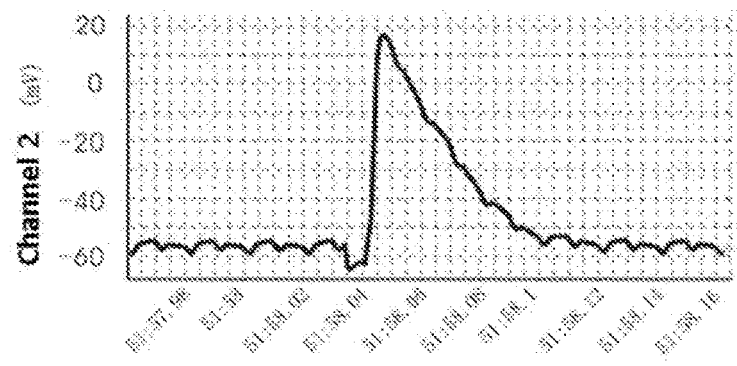
Figure 2C:
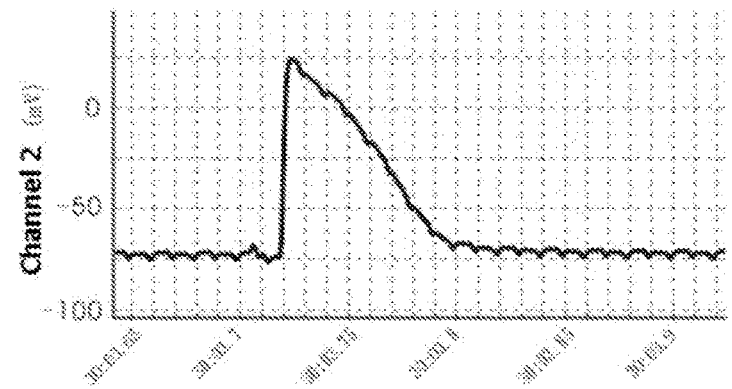
Figure 2D:
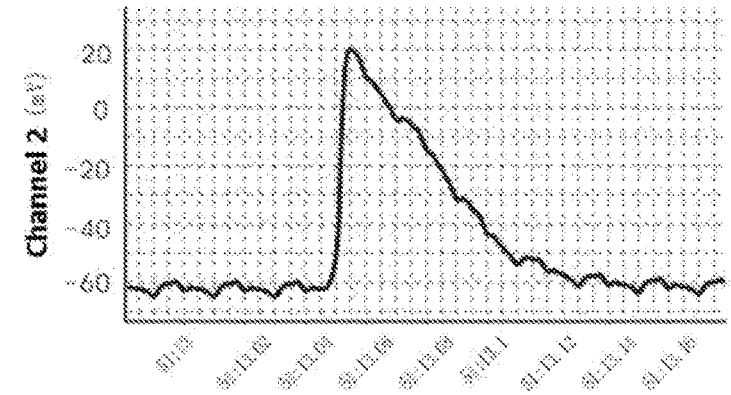

The following compounds are preferable in the present invention.

TABLE 1

Preferable compounds in the present invention

| | |
|---|---|
| Compound 369 (Example 1) | (3β,5α)-4,4,14-trimethyl-3-(methylamino)-9,19-cyclopregnan-16-en-20-one |
| Compound 384 (Example 3) | (3β,5α)-4,4,14-trimethyl-3-(methylamino)-9,19-cyclopregnan-16-en-20-one oxime |
| Compound 398 (Example 4) | (3β,5α)-4,4,14-trimethyl-3-(methylamino)-20-methoxyimino-9,19-cyclopregnan-16-ene |
| Compound 385 (Example 8) | (3β,5α)-4,4,14-trimethyl-21-hydroxy-3-(methylamino)-9,19-cyclopregnan-16-en-20-one |
| Compound 427 (Example 9) | (3β,5α)-4,4,14-trimethyl-21-acetoxy-3-(methylamino)-9,19-cyclopregnan-16-en-20-one |
| Compound 522 (Example 10) | (3β,5α)-4,4,14-trimethyl-3-(methylamino)-21-(3-carboxypropionyloxy)-9,19-cyclopregnan-16-en-20-one hydrochloride |
| Compound 570 (Example 11) | (3β,5α)-4,4,14-trimethyl-3-(methylamino)-21-(2-carboxybenzoyloxy)-9,19-cyclopregnan-16-en-20-one hydrochloride |
| Compound 489 (Example 12) | (3β,5α)-4,4,14-trimethyl-3-(methylamino)-21-(benzoyloxy)-9,19-cyclopregnan-16-en-20-one |

TABLE 1-continued

Preferable compounds in the present invention

| | |
|---|---|
| Compound 397 (Example 16) | (3β,5α)-4,4,14-trimethyl-3-(methylethylamino)-9,19-cyclopregnan-16-en-20-one |
| Compound 399a (Example 17) | (3β,5α)-4,4,14-trimethyl-21-hydroxy-3-(dimethylamino)-9,19-cyclopregnan-16-en-20-one |
| Compound 409 (Example 18) | (3β,5α)-4,4,14-trimethyl-3-(methylcyclopropylamino)-9,19-cyclopregnan-16-en-20-one |
| Compound 387 (Example 19) | (3β,5α)-4,4,14-trimethyl-16-fluoro-3-(methylamino)-9,19-cyclopregnan-16-en-20-one |
| Compound 383a (Example 20) | (3β,5α)-4,4,14,16-tetramethyl-3-(methylamino)-9,19-cyclopregnan-16-en-20-one |

The compound of formula (I) in the present invention may form a pharmaceutically acceptable salt together with various organic or inorganic acids such as: hydrochloric acid, hydrobromic acid, methanesulfonic acid, isethionic acid, sulfuric acid, acetic acid, trifluoroacetic acid, maleic acid, benzenesulfonic acid, toluenesulfonic acid, nitric acid, phosphoric acid, boric acid, tartaric acid, citric acid, succinic acid, benzoic acid, ascorbic acid, salicylic acid or the like.

Further, the compound of formula (I) in the present invention may form a salt together with an alkali metal such as sodium, potassium, or lithium, may form a salt together with an alkaline earth metal such as calcium or magnesium, and may form a salt together with an organic base such as dicyclohexyl amine, tributylamine, pyridine, and an amino acid (e.g., arginine, lysine) or the like.

The compound of the present invention may be prepared by the following method:

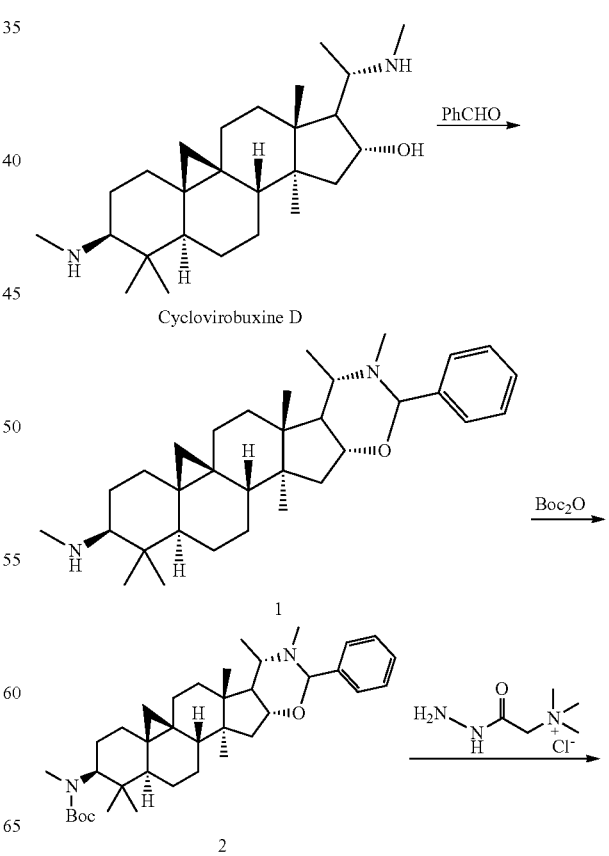

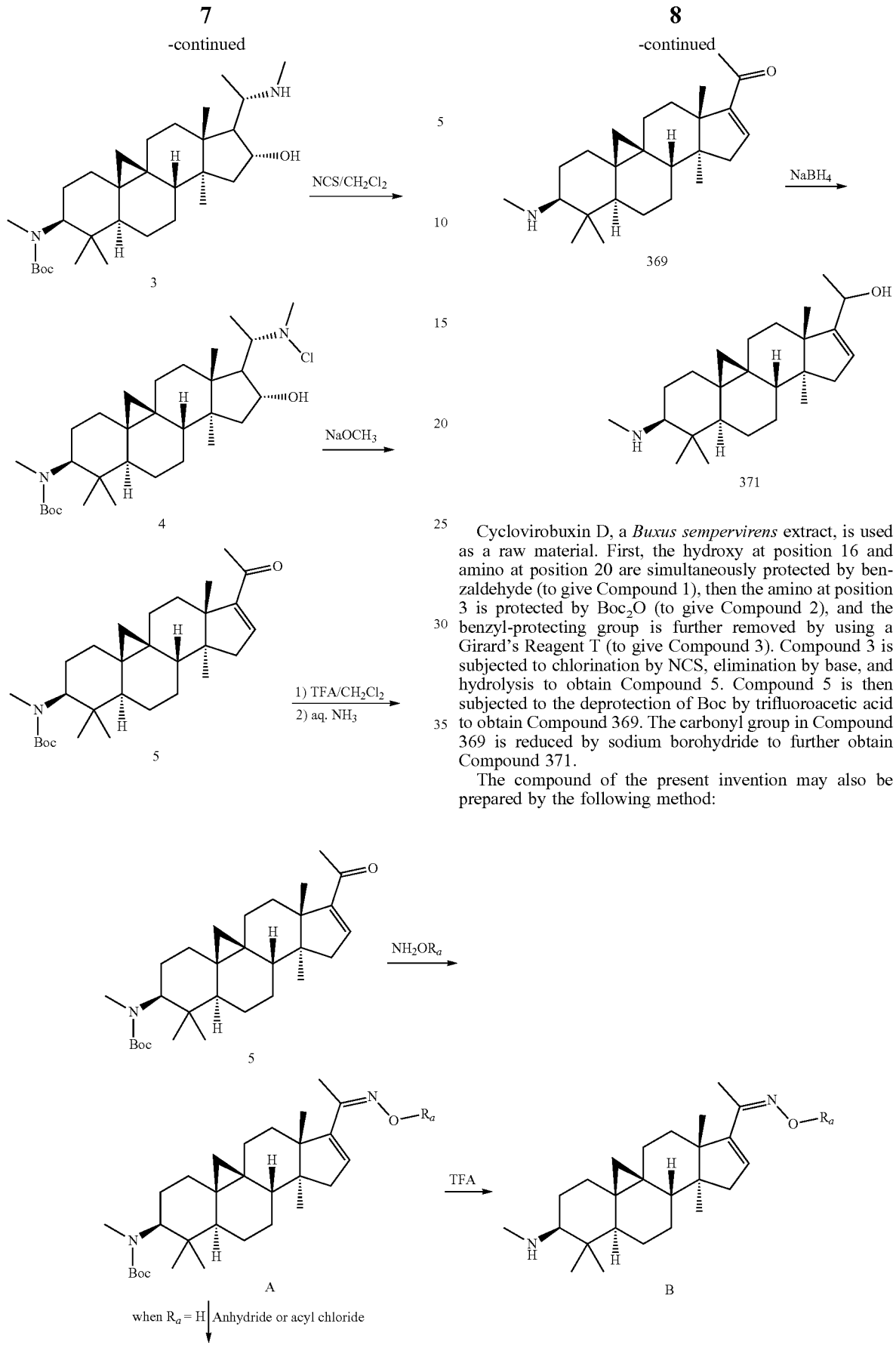

Cyclovirobuxin D, a *Buxus sempervirens* extract, is used as a raw material. First, the hydroxy at position 16 and amino at position 20 are simultaneously protected by benzaldehyde (to give Compound 1), then the amino at position 3 is protected by Boc$_2$O (to give Compound 2), and the benzyl-protecting group is further removed by using a Girard's Reagent T (to give Compound 3). Compound 3 is subjected to chlorination by NCS, elimination by base, and hydrolysis to obtain Compound 5. Compound 5 is then subjected to the deprotection of Boc by trifluoroacetic acid to obtain Compound 369. The carbonyl group in Compound 369 is reduced by sodium borohydride to further obtain Compound 371.

The compound of the present invention may also be prepared by the following method:

-continued

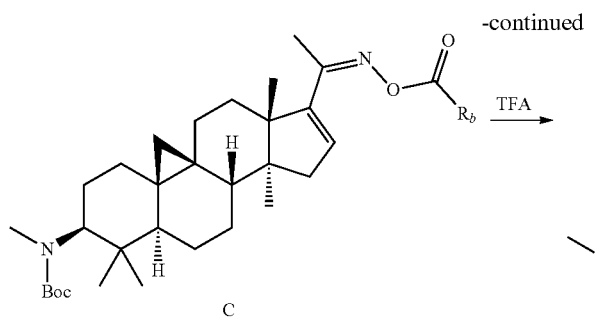

C

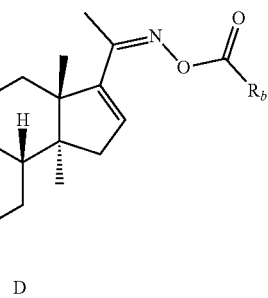

D

Compound 5 is reacted with a hydroxylamine compound ($NH_2OR_a$) (such as $NH_2OH$, $NH_2OCH_3$, or $NH_2OC_2H_5$) to generate a substituted or unsubstituted oxime (a compound of general formula A), which is subjected to the deprotection of Boc by trifluoroacetic acid to obtain a compound of general formula B, wherein $R_a$ is hydrogen, or substituted or unsubstituted $C_1$-$C_4$ alkyl.

In addition, when the substituent $R_a$ is hydrogen, the compound of general formula A may be reacted with an anhydride (acetic anhydride, propionic anhydride, benzoic anhydride, succinic anhydride, glutaric anhydride, maleic anhydride, phthalic anhydride or the like) or an acyl chloride (acetyl chloride, propionyl chloride, cyclopropyl chloride, butyryl chloride, pivaloyl chloride, benzoyl chloride or the like) to generate a compound of general formula C, which is deprotected by an acid to obtain a compound of general formula D, wherein $R_b$ is a substituted or unsubstituted group selected from: $C_1$-$C_{10}$ alkyl, $C_3$-$C_{10}$ cycloalkyl, $C_2$-$C_{10}$ alkenyl, or $C_6$-$C_{12}$ aryl.

The compound of the present invention may also be prepared by the following method:

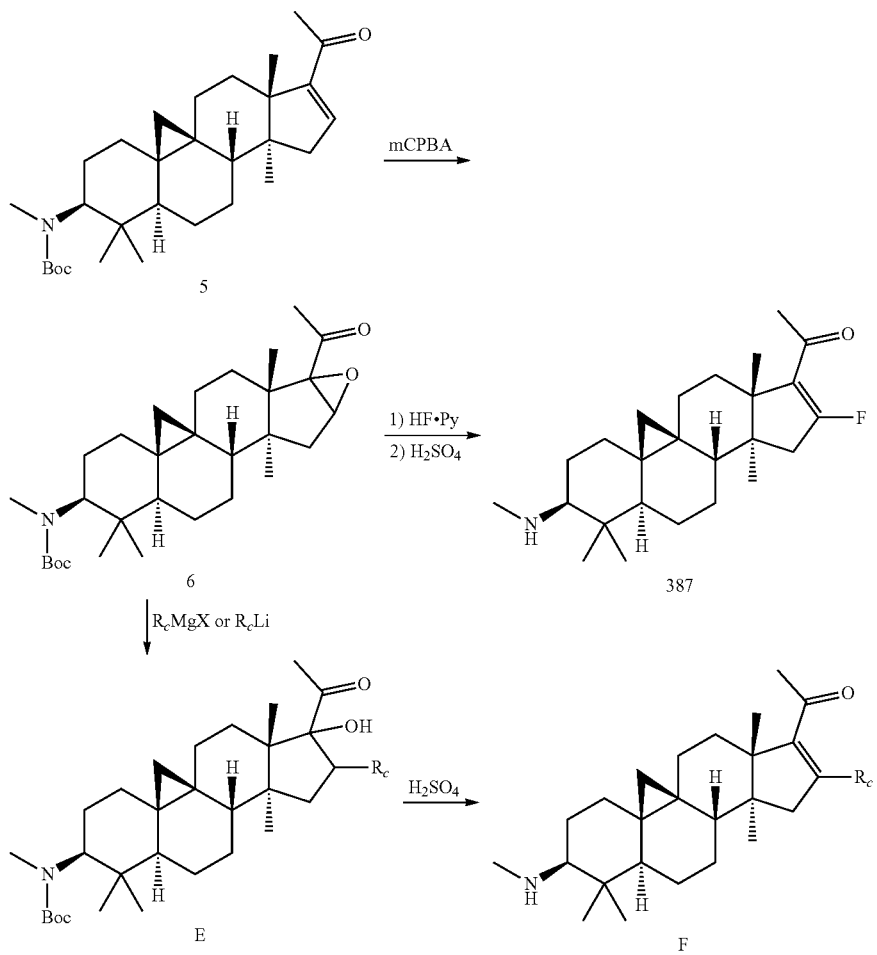

The double bond in Compound 5 is epoxidized by m-chloroperoxybenzoic acid (mCPBA) to generate Compound 6. Compound 6 is then subjected to the fluorination by a fluorinating agent such as hydrogen fluoride-pyridine, the deprotection of Boc under an acidic condition, and the elimination of hydroxy to obtain Compound 387.

Compound 6 is reacted with a Grignard reagent or a lithium reagent of alkyl or cycloalkyl ($R_cMgX$ or $R_cLi$) to generate a compound of general formula E, which is then subjected to the deprotection of Boc under an acidic condition and the elimination of hydroxy to obtain a compound of general formula F, wherein $R_c$ is substituted or unsubstituted $C_1$-$C_6$ alkyl, or substituted or unsubstituted $C_3$-$C_6$ cycloalkyl.

The compound of the present invention may also be prepared by the following method:

Compound 6 is oxidized by iodobenzene diacetate to generate Compound 7. The hydroxy of Compound 7 is then subjected to the acetylation to obtain Compound 8. The epoxy group of Compound 8 is then reduced by chromium dichloride to generate Compound 9 having a double bond. Finally, Compound 427 and Compound 385 are prepared by removing different protecting groups from Compound 9.

The hydroxy in Compound 10 obtained from mere deprotection of hydroxy-protecting group may react with various active reagents, like forming an ester group (a compound of general formula G, wherein $R_d$ is a substituted or unsubstituted group selected from: $C_1$-$C_{10}$ alkyl, $C_3$-$C_{10}$ cycloalkyl,

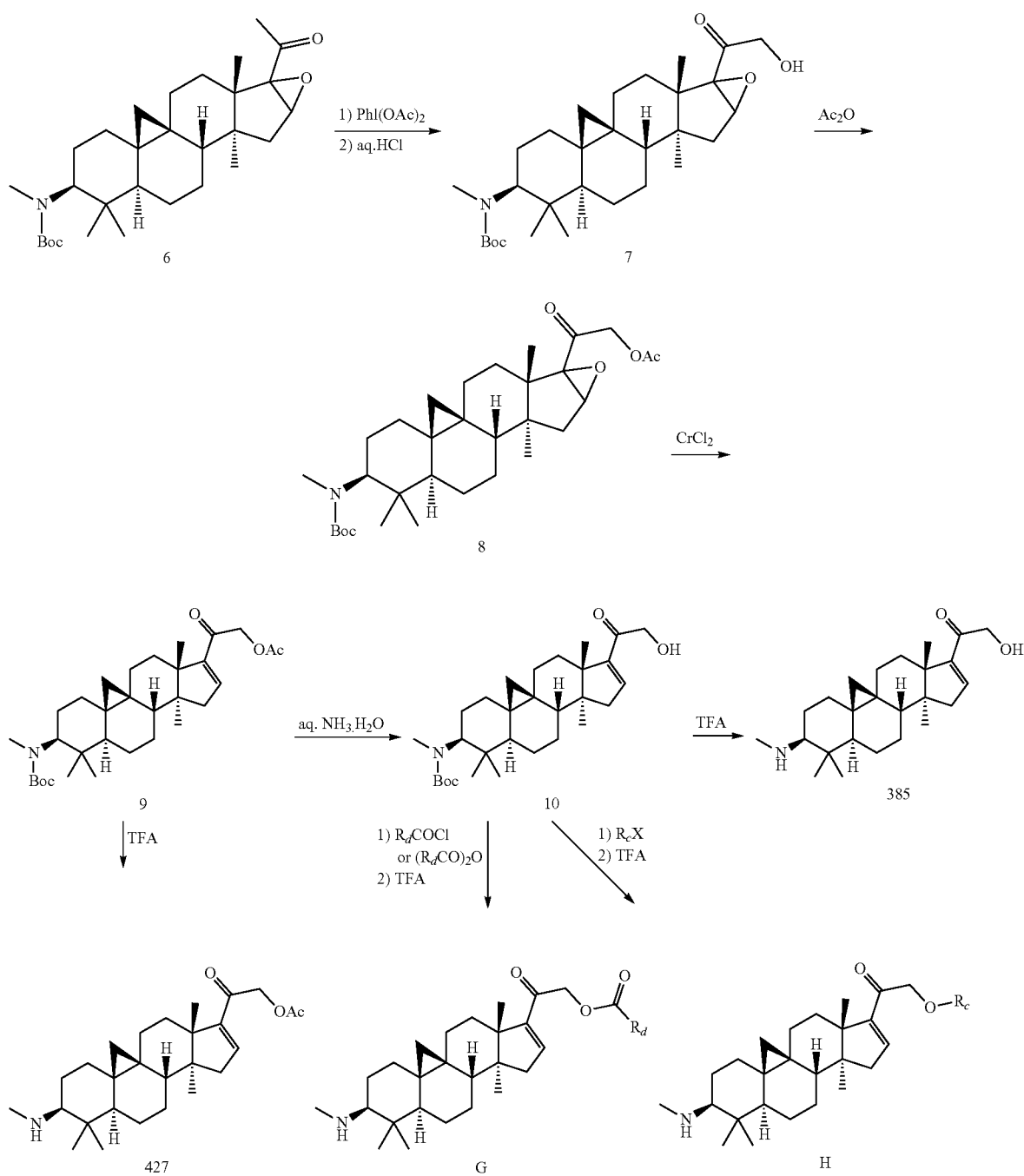

$C_2-C_{10}$ alkenyl, $C_6-C_{12}$ aryl, or heteroaryl) with an acyl chloride or an anhydride, or forming an alkoxy group with an alkyl halide.

The compound of the present invention may also be prepared by the following methods:

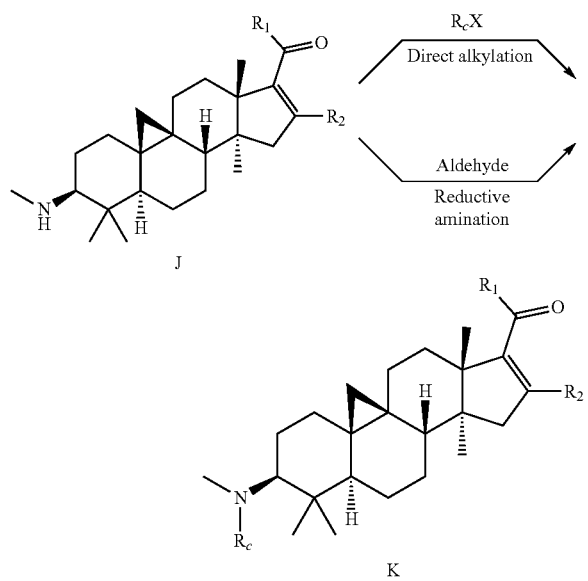

A methylamino compound (a compound of general formula J) is directly alkylated by an alkyl halide $R_cX$ or subjected to reductive amination reaction with an aldehyde, to obtain a methylamino substituted compound (a compound of general formula K, wherein $R_c$ is substituted or unsubstituted $C_1-C_6$ alkyl or $C_3-C_6$ cycloalkyl).

The compound of formula (I) in the present invention may be mixed with a pharmaceutically acceptable carrier to prepare various pharmaceutical compositions. The compound of formula (I) can be prepared into a preventive and therapeutic medicament for the cardiovascular and/or cerebrovascular disease in a solid dosage form (such as tablets, pills, capsules, or various corresponding sustained-release and controlled-release formulations or the like) by a conventional method after mixed with a common auxiliary additive (such as a disintegrant, an excipient, a lubricant, a binder, a filler or the like) which are acceptable in an oral preparation; can be prepared into a preventive and therapeutic medicament for the cardiovascular and/or cerebrovascular disease in a liquid dosage form (such as aqueous solutions, syrups or the like) by a corresponding conventional method after mixed with a commonly used surfactant (such as a solubilizer, an emulsifier, a wetting agent, foaming or a defoaming agent), a diluent, a preservative, a stabilizer, a flavoring agent, a thickening agent or the like; also can be prepared into a preventive and therapeutic medicament for the cardiovascular and/or cerebrovascular disease in a dosage form of corresponding intramuscular or intravenous injection through the combination and operation with a suitable solvent and an additive commonly used in injections.

The administration method for dosing may be selected from oral, intranasal, rectal, transdermal, or injection administration, which is administrated in a form of solid, semi-solid, lyophilized powder, or liquid agent, for example, tablets, suppositories, pills, soft or hard capsules, powders, solutions, suspensions, aerosols, and the like.

The pharmacodynamic testing results of the compound of the present invention show that the compound of the present invention has excellent pharmacodynamic and pharmacological activities against arrhythmia, myocardial anoxia, myocardial ischemia, and heart failure. In addition, the compound of the present invention also has good pharmacokinetic characteristics, suitable half-life and good safety.

Accordingly, the present invention also provides the use of a compound of formula (I), an optical isomer thereof or a pharmaceutically acceptable salt thereof as an active ingredient in the manufacture of a pharmaceutical composition for preventing or treating cardiovascular and/or cerebrovascular diseases or disorders, wherein the diseases or disorders are selected from tachyarrhythmia (including atrial flutter and atrial fibrillation, supraventricular tachycardia, ventricular premature beat, ventricular tachycardia, and ventricular fibrillation), coronary atherosclerotic heart disease (including stable angina pectoris and unstable angina pectoris, acute coronary syndrome, and myocardial infarction), asymptomatic myocardial ischemia and ischemic cardiomyopathy, heart failure (including acute and chronic heart failure), and their complications.

The cardiovascular and/or cerebrovascular diseases or disorders are preferably selected from atrial fibrillation, ventricular premature beat, ventricular tachycardia, ventricular fibrillation, angina pectoris (including stable and unstable angina pectoris), acute coronary syndrome, myocardial infarction, and heart failure (including acute and chronic heart failure).

EXAMPLES

The preparation method of the compound according to the present invention is particularly illustrated via the examples below. It should be pointed out that the technical solutions according to the present invention are not limited to the examples.

Example 1

(3β,5α)-4,4,14-trimethyl-3-(methylamino)-9,19-cyclopregnan-16-en-20-one (Compound 369)

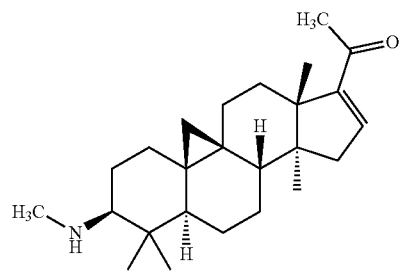

Step 1: Synthesis of Intermediate 1:

Cyclovirobuxin D (544 g, 1.35 mol) was dissolved in 4 L ethanol. Benzaldehyde (286.4 g, 2.7 mol) was added therein, stirred and heated under reflux to react for 5 h. The mixture was cooled to room temperature and filtered, and the filter cake was rinsed with a small amount of ethanol to have no odour of benzaldehyde. The resultant filter cake was dried in vacuo at 50° C., to obtain 550 g of a white solid (i.e., Intermediate 1) with a yield of 82.9%. ESI(+)m/z: 491.4 $[M+H]^+$.

Step 2: Synthesis of Intermediate 2:

Intermediate 1 mentioned above (550 g, 1.12 mol) was dissolved in 2.4 L dichlormethane. 100 ml of a dichlormethane solution containing Boc$_2$O (361 g, 1.658 mol) was added dropwise therein under the monitor of TLC until the raw materials disappeared (developing solvent: dichlormethane/methanol=10:1, V/V). The reaction mixture was concentrated in vacuo to dryness. Then 2 L methanol was added therein and stirred for 15 min, and filtered. The filter cake was rinsed with a small amount of methanol. The resultant solid was dried in vacuo at 50° C., to obtain 580 g of a white solid (i.e., Intermediate 2) with a yield of 87.6%. ESI(+)m/z: 591.4 [M+H]$^+$.

Step 3: Synthesis of Intermediate 3:

Intermediate 2 mentioned above (580 g, 0.981 mol) was suspended in a solvent of 1.5 L dichlormethane and 1.5 L methanol. A Girard's Reagent (Girard's Reagent T, 180 g, 1.072 mol) was added therein. The mixture was heated and refluxed until the solution was clear. The mixture was monitored using TLC until the raw materials disappeared (developing solvent: dichlormethane/methanol=20:1, V/V). The reaction mixture was evaporated in vacuo to dryness. To the residue was added 1 L ethyl acetate and 1 L water. The mixture was stirred for 10 min and filtered. The filter cake was then washed with 2 L water. The resultant solid was dried in vacuo at 50° C., to obtain 484 g of a white solid (i.e., Intermediate 3) with a yield of 98%. ESI(+)m/z: 503.4 [M+H]$^+$.

Step 4: Synthesis of Intermediate 4:

Intermediate 3 mentioned above (484 g, 0.964 mol) was dissolved in 11 L dichlormethane under the protection of argon, and cooled to around 0° C. N-chlorosuccinimide (NCS) (142 g, 1.06 mol) was added in batches, and stirred and reacted for 2 h. The reaction mixture was washed with water for three times, dried over anhydrous magnesium sulfate, and filtered. The filtrate was concentrated in vacuo to dryness, to obtain 540 g of a solid (i.e., Intermediate 4) with a yield of 97%.

Step 5: Synthesis of Intermediate 5:

Intermediate 4 mentioned above (360 g, 0.67 mol) was dissolved in 4 L anhydrous methanol under the protection of argon, and sodium methoxide (180 g, 3.33 mol) was added. The mixture was refluxed and reacted for 4 h, and cooled to room temperature. The pH was adjusted to 6 by 4M aqueous hydrochloric acid. Methanol was removed by distillation in vacuo. 500 ml ethyl acetate and 200 ml water were added to the residue, filtered and separated. The layer of ethyl acetate was purified via column chromatography, to obtain 145 g of a white solid (i.e., Intermediate 5) with a yield of 46%. ESI(+)m/z: 470.3 [M+H]$^+$, 492.3 [M+Na]$^+$, 414.3 [de-tert-butyl].

Step 6: Synthesis of Compound 369:

Intermediate 5 mentioned above (145 g, 0.304 mol) was dissolved in 1 L dichlormethane, and 300 ml trifluoroacetic acid was added therein. The mixture was stirred and reacted until no raw material is remained. The trifluoroacetic acid and dichlormethane were removed by distillation in vacuo to obtain a trifluoroacetate of the title compound. The resultant trifluoroacetate was dissolved by 1 L dichlormethane, and the pH was adjusted to 9 by conc. aqueous ammonia. The mixture was separated, and the organic layer was washed with water to neutrality, dried over anhydrous magnesium sulfate, and filtered. The filtrate was subjected to rotary evaporation to dryness. The resultant residue was recrystallized using 300 ml ethyl acetate, to obtain 105 g of the title compound with a yield of 92%.

$^1$H-NMR (CDCl$_3$, 500M): δ (ppm): 6.65 (1H, m, =CH), 2.47 (3H, s, CH$_3$NH), 2.27 (3H, s, CH$_3$CO), 2.20-2.18 (1H, m), 2.16-1.90 (5H, m), 1.90-1.42 (4H, m), 1.40-1.25 (4H, m), 1.21 (3H, s, CH$_3$), 1.20-1.03 (2H, m), 0.99 (3H, s, CH$_3$), 0.97 (3H, s, CH$_3$), 0.90-0.73 (1H, m), 0.79 (3H, s, CH$_3$), 0.65 (1H, d), 0.35 (1H, d);

$^{13}$C-NMR (CDCl$_3$, 300M): δ (ppm): 196.86, 152.70, 143.81, 68.54, 50.64, 48.83, 48.63, 46.08, 43.03, 39.89, 35.62, 32.67, 31.38, 27.17, 27.09, 26.83, 26.66, 26.44, 26.16, 25.80, 22.33, 21.08, 20.52, 19.78, 15.04;

HR-ESI(+)m/z: found 370.3211.

Step 7: Preparation of a Single Crystal of the Trifluoroacetate of Compound 369:

The trifluoroacetate of the title compound obtained in the above step 6 was dissolved by acetone, and slowly crystallized at room temperature, to obtain a single crystal of the trifluoroacetate of the title compound. The X ray-single crystal diffraction data are shown in Table 2, and the spectrogram is shown in FIG. 1.

TABLE 2

| Crystal data and Structure refinement | |
|---|---|
| Identification code | b |
| Empirical formula | C27 H40 F3 N O3 |
| Formula weight | 483.60 |
| Temperature | 293(2) K |
| Wavelength | 0.71073 A |
| Crystal system, space group | Orthorhombic, P212121 |
| Unit cell dimensions | a = 15.999(3) A   alpha = 90 deg. |
| | b = 19.709(4) A   beta = 90 deg. |
| | c = 8.3140(17) A  gamma = 90 deg. |
| Volume | 2621.6(9) A^3 |
| Z, Calculated density | 4, 1.225 Mg/m^3 |
| Absorption coefficient | 0.093 mm^-1 |
| F(000) | 1040 |
| Crystal size | 0.30 × 0.20 × 0.10 mm |
| Theta range for data collection | 1.64 to 25.40 deg. |
| Limiting indices | 0 ≤ h ≤ 19, -23 ≤ k ≤ 23, 0 ≤ l ≤ 10 |
| Reflections collected/unique | 5325/4806 [R(int) = 0.0338] |
| Completeness to theta = 25.40 | 99.8% |
| Absorption correction | Psi-scan |
| Max. and mix. transmission | 0.9908 and 0.9727 |
| Refinement method | Full-matrix least-squares on F^2 |
| Data/restraints/parameters | 4806/1/283 |
| Goodness-of-fit on F^2 | 1.220 |
| Final R indices [I > 2sigma(I)] | R1 = 0.1111, wR2 = 0.2141 |
| R indices (all data) | R1 = 0.2167, wR2 = 0.2524 |
| Absolute structure parameter | 0(3) |
| Largest diff peak and hole | 0.759 and -0.541 e.A^-3 |

Example 2

(3β,5α)-4,4,14-trimethyl-3-(methylamino)-9,19-cyclopregnan-16-en-20-ol (Compound 371)

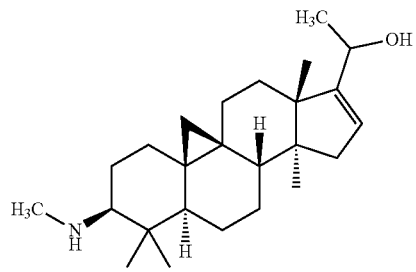

The title compound in Example 1 (3.7 g, 10 mmol) was dissolved in 20 ml methanol, and sodium borohydride (1.51 g, 40 mmol) was added in batches. The mixture was stirred and reacted under the monitor of TLC until no raw material is remained. 1N aqueous hydrochloric acid was added to the reaction mixture such that the pH was adjusted to 8-9. The solvent was removed by distillation. The resultant residue was purified via column chromatography using dichlormethane/methanol, to obtain 3 g of the title compound with a yield of 92%.

$^1$H-NMR (CDCl$_3$, 500M): δ (ppm): 5.92 (1H, s, =CH), 4.10 (1H, m, CHOH), 2.60 (3H, s, CH$_3$NH), 2.43-2.49 (1H, m), 2.31-2.36 (1H, m), 1.98-2.15 (4H, m), 1.63-1.88 (4H, m), 1.52-1.58 (1H, m), 1.48 (3H, s, CH$_3$CHOH), 1.35-1.45 (3H, m), 1.19 (3H, s, CH$_3$), 1.12 (3H, s, CH$_3$), 1.05-1.19 (2H, m), 0.96 (3H, s, CH$_3$), 0.94 (3H, s, CH$_3$), 0.78-0.88 (1H, m), 0.66 (1H, d), 0.58 (1H, d);

ESI(+)m/z: 372.4 (M+H)$^+$.

Example 3

(3β,5α)-4,4,14-trimethyl-3-(methylamino)-9,19-cyclopregnan-16-en-20-one oxime (Compound 384)

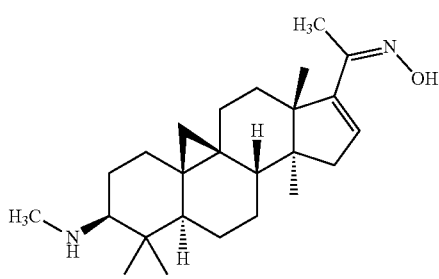

The title compound in Example 1 (7.5 g, 20.3 mmol) was dissolved in 40 ml ethanol, and hydroxylamine hydrochloride (2.8 g, 40.3 mmol) was added therein. After stirring until the solution is clear, triethylamine (4.5 g, 47.55 mol) was added. The mixture was heated to reflux, and reacted under the monitor of TLC until no raw material is remained. Ethanol was removed by distillation in vacuo. Dichlormethane and water were added to the residue, dissolved and separated. The layer of dichlormethane was washed with water, dried, and filtered. The filtrate was subjected to rotary evaporation to dryness, to obtain 7 g of the title compound as a solid with a yield of 90%.

$^1$H-NMR (CDCl$_3$, 500M): δ (ppm): 5.85 (1H, s, =CH), 2.46 (3H, s, CH$_3$NH), 2.26-2.29 (1H, m), 2.22-2.27 (1H, m), 2.08 (3H, s, CH$_3$CNOH), 1.95-2.01 (4H, m), 1.68-1.90 (4H, m), 1.50-1.58 (1H, m), 1.38-1.48 (3H, m), 1.29 (3H, s, CH$_3$), 1.20 (3H, s, CH$_3$), 1.05-1.15 (2H, m), 0.96 (3H, s, CH$_3$), 0.94 (3H, s, CH$_3$), 0.78-0.88 (1H, m), 0.66 (1H, d), 0.62 (1H, d);

$^{13}$C-NMR (CDCl$_3$, 500M): δ (ppm): 151.48, 149.71, 129.13, 77.24, 76.99, 76.74, 69.51, 51.43, 48.86, 48.38, 47.58, 42.85, 39.80, 35.37, 32.10, 27.32, 27.03, 26.92, 26.31, 25.75, 23.26, 21.71, 20.71, 20.51, 15.56, 11.03;

HR-ESI(+): found 385.3331.

Example 4

(3β,5α)-4,4,14-trimethyl-3-(methylamino)-20-methoxyimino-9,19-cyclopregnan-16-ene (Compound 398)

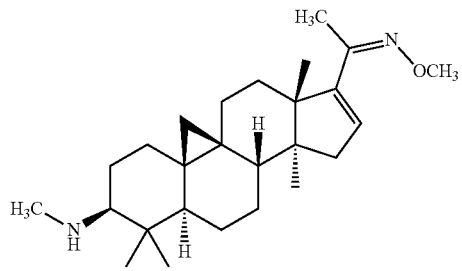

Identical to the preparation process in Example 3, the title compound in Example 1 (7.4 g, 20 mmol), O-methylhydroxylamine hydrochloride (2.8 g, 40.3 mmol), triethylamine (4.5 g, 47.55 mol) were used to obtain 7 g of the title compound as a solid with a yield of 88%. ESI(+)m/z: 399.4 (M+H)$^+$.

$^1$H-NMR (CDCl$_3$, 500M): δ (ppm): 5.99 (1H, s, =CH), 4.23 (3H, s, CH$_3$ON=), 2.52 (3H, s, CH$_3$NH), 2.46-2.49 (1H, m), 2.22-2.27 (1H, m), 2.06 (3H, s, CH$_3$C=N), 1.95-2.02 (4H, m), 1.68-1.90 (4H, m), 1.50-1.58 (1H, m), 1.35-1.46 (3H, m), 1.28 (3H, s, CH$_3$), 1.21 (3H, s, CH$_3$), 1.05-1.15 (2H, m), 0.96 (3H, s, CH$_3$), 0.94 (3H, s, CH$_3$), 0.79-0.88 (1H, m), 0.67 (1H, d), 0.63 (1H, d).

Example 5

(3β,5α)-4,4,14-trimethyl-3-(methylamino)-20-[(3-carboxypropionyloxy)imino)]-9,19-cyclopregnan-16-ene (Compound 484)

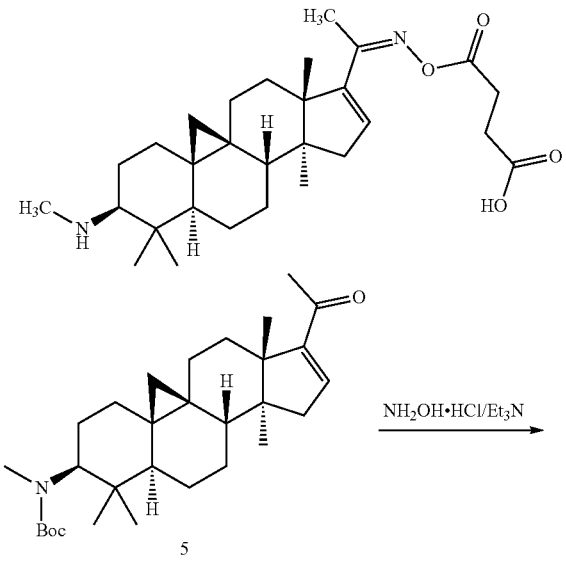

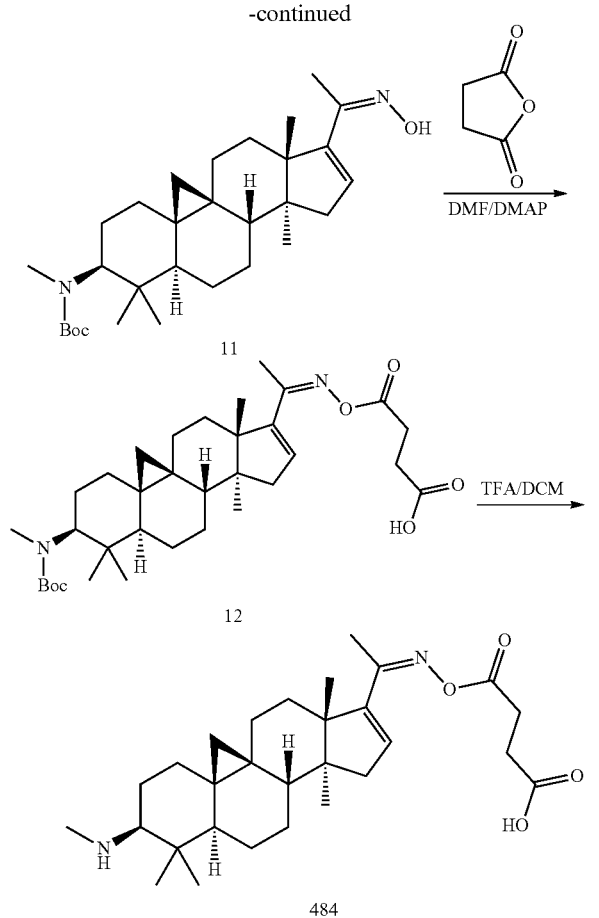

Step 1: Synthesis of Intermediate 11:

The product in step 5 of Example 1 (Intermediate 5, 4.7 g, 10 mmol) was dissolved in 30 ml ethanol, and hydroxylamine hydrochloride (2.78 g, 40 mmol) was added therein. After stirring until the solution is clear, triethylamine (4.5 g, 44.75 mol) was added. The mixture was heated to reflux, and reacted under the monitor of TLC until no raw material is remained. Ethanol was removed by distillation in vacuo. Dichlormethane and water were added to the residue, and separated. The layer of dichlormethane was washed with water, dried, and filtered. The filtrate was subjected to rotary evaporation to dryness, to obtain 4.5 g of a solid (i.e., Intermediate 11).

Step 2: Synthesis of Intermediate 12:

Intermediate 11 mentioned above (4.5 g, 7.28 mmol) was dissolved in DMF (50 ml). Succinic anhydride (0.9 g, 9 mmol) and 4-dimethylaminopyridine (1.22 g, 10 mmol) were added therein. The mixture was heated to 80° C., and reacted under the monitor of TLC until no raw material is remained. The mixture was cooled to room temperature. The reaction mixture was poured into ice water. The solid was precipitated out, filtered, washed with water, and dried to obtain 4.1 g of a solid (i.e., Intermediate 12).

Step 3: Synthesis of Compound 484:

Intermediate 12 mentioned above (4.1 g, 7 mmol) was dissolved in 20 ml dichlormethane, and 7 ml trifluoroacetic acid was added therein. The mixture was stirred and reacted under the monitor of TLC until no raw material is remained. The trifluoroacetic acid and dichlormethane were removed by distillation in vacuo. The residue was dissolved by 20 ml dichlormethane, and the pH was adjusted to 8 by conc. aqueous ammonia. The mixture was separated, and the organic layer was washed with water to neutrality, dried over anhydrous magnesium sulfate, and filtered. The filtrate was subjected to rotary evaporation to dryness. The resultant residue was recrystallized using 300 ml ethyl acetate, to obtain 3 g of the title compound. ESI(+)m/z: 485.4 (M+H)+.

$^1$H-NMR (CDCl$_3$, 500M): δ (ppm): 6.20 (1H, s, =CH), 2.65-2.68 (2H, m, CH$_2$COOH), 2.60-2.63 (2H, m, CH$_2$CO), 2.48 (3H, s, CH$_3$NH), 236-2.39 (1H, m), 2.22-2.27 (1H, m), 2.06 (3H, s, CH$_3$C=N), 1.96-2.02 (4H, m), 1.66-1.90 (4H, m), 1.50-1.58 (1H, m), 1.35-1.46 (3H, m), 1.28 (3H, s, CH$_3$), 1.21 (3H, s, CH$_3$), 1.05-1.15 (2H, m), 0.96 (3H, s, CH$_3$), 0.94 (3H, s, CH$_3$), 0.79-0.88 (1H, m), 0.66 (1H, d), 0.60 (1H, d).

Example 6

(3β,5α)-4,4,14-trimethyl-3-(methylamino)-20-[(acetoxy)imino)]-9,19-cyclopregnan-16-ene (Compound 426)

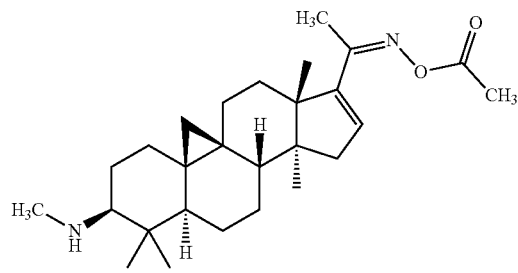

Identical to the preparation process in steps 2 and 3 of Example 5, acetic anhydride was used to replace the succinic anhydride, so as to obtain the title compound. ESI(+)m/z: 427.3 (M+H)$^+$.

$^1$H-NMR (CDCl$_3$, 500M): δ (ppm): 5.98 (1H, s, =CH), 2.47 (3H, s, CH$_3$NH), 2.36-2.40 (1H, m), 2.22-2.27 (1H, m), 2.10 (3H, s, CH$_3$CO), 2.06 (3H, s, CH$_3$C=N), 1.95-2.02 (4H, m), 1.68-1.90 (4H, m), 1.50-1.58 (1H, m), 1.35-1.46 (3H, m), 1.28 (3H, s, CH$_3$), 1.21 (3H, s, CH$_3$), 1.05-1.15 (2H, m), 0.96 (3H, s, CH$_3$), 0.94 (3H, s, CH$_3$), 0.79-0.88 (1H, m), 0.66 (1H, d), 0.64 (1H, d).

Example 7

(3β,5α)-4,4,14-trimethyl-3-(methylamino)-20-[(benzoyloxy)imino)]-9,19-cyclopregnan-16-ene (Compound 488)

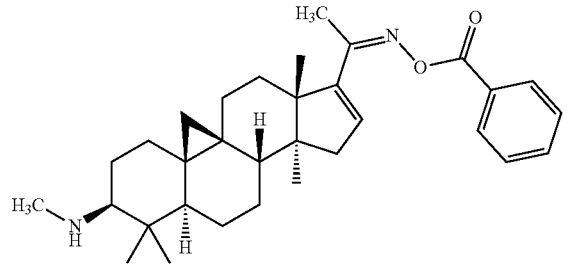

Identical to the preparation process in steps 2 and 3 of Example 5, benzoic anhydride was used to replace the succinic anhydride, so as to obtain the title compound. ESI(+)m/z: 489.4 (M+H)+.

¹H-NMR (CDCl₃, 500M): δ (ppm): 8.15 (1H, s), 8.13 (1H, s), 7.60 (1H, s), 7.48 (1H, s), 7.46 (1H, s), 5.88 (1H, s, =CH), 2.47 (3H, s, CH₃NH), 2.36-239 (1H, m), 2.22-2.27 (1H, m), 2.06 (3H, s, CH₃C=N), 1.96-2.02 (4H, m), 1.66-1.90 (4H, m), 1.50-1.58 (1H, m), 1.35-1.46 (3H, m), 1.28 (3H, s, CH₃), 1.21 (3H, s, CH₃), 1.05-1.15 (2H, m), 0.96 (3H, s, CH₃), 0.94 (3H, s, CH₃), 0.79-0.88 (1H, m), 0.66 (1H, d), 0.62 (1H, d).

Example 8

(3β,5α)-4,4,14-trimethyl-21-hydroxy-3-(methylamino)-9,19-cyclopregnan-16-en-20-one (Compound 385)

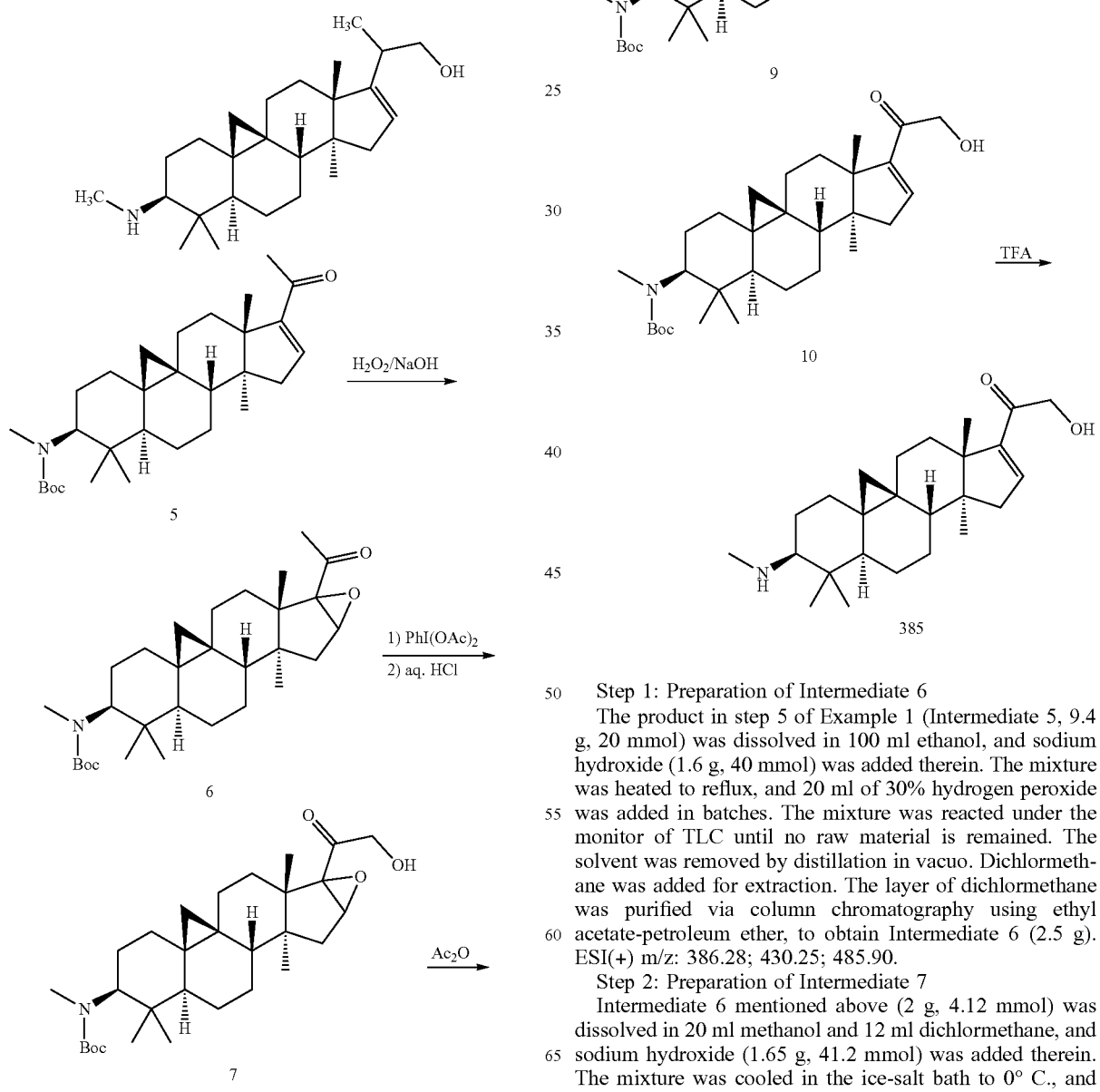

Step 1: Preparation of Intermediate 6

The product in step 5 of Example 1 (Intermediate 5, 9.4 g, 20 mmol) was dissolved in 100 ml ethanol, and sodium hydroxide (1.6 g, 40 mmol) was added therein. The mixture was heated to reflux, and 20 ml of 30% hydrogen peroxide was added in batches. The mixture was reacted under the monitor of TLC until no raw material is remained. The solvent was removed by distillation in vacuo. Dichlormethane was added for extraction. The layer of dichlormethane was purified via column chromatography using ethyl acetate-petroleum ether, to obtain Intermediate 6 (2.5 g). ESI(+) m/z: 386.28; 430.25; 485.90.

Step 2: Preparation of Intermediate 7

Intermediate 6 mentioned above (2 g, 4.12 mmol) was dissolved in 20 ml methanol and 12 ml dichlormethane and sodium hydroxide (1.65 g, 41.2 mmol) was added therein. The mixture was cooled in the ice-salt bath to 0° C., and iodobenzene diacetate (2.12 g, 6.59 mmol) was added therein. The mixture was stirred and reacted under the monitor of TLC until no raw material is remained. The solvent was removed by distillation in vacuo. The residue was dissolved by adding water and dichlormethane. The pH was adjusted to around 7, and the mixture was separated. The organic layer was washed with water, dried, filtered, and subjected to rotary evaporation to dryness. The residue was pulped by a small amount of petroleum ether and subjected to suction filtration, to obtain a white solid. The resultant while solid was dissolved in 20 ml acetone, and 5 ml of 1M aqueous HCl was added therein. The mixture was stirred until the reaction was completed. 50 ml water was added to the reaction mixture. The mixture was filtered and dried to obtain 920 mg of a off-white solid (i.e., Intermediate 7). ESI(+) m/z: 446.28; 502.04.

Step 3: Preparation of Intermediate 8

Intermediate 7 mentioned above (920 mg, 1.83 mmol) was dissolved in 5 ml pyridine, and 1 ml acetic anhydride was added therein. The mixture was stirred at room temperature and reacted under the monitor of TLC until no raw material is remained. Dichlormethane was added to the reaction mixture for dilution. The organic layer was washed with 5% aqueous citric acid to weak acidity, washed with water to neutrality, dried, and filtered. The filtrate was subjected to rotary evaporation to dryness, to obtain 1.09 g of a white solid (i.e., Intermediate 8). ESI(+) m/z: 444.30; 488.28.

Step 4: Preparation of Intermediate 9

Intermediate 8 mentioned above (1.09 g, 1.83 mmol) was dissolved in 60 ml acetone under the protection of argon. The mixture was cooled to 0° C., and 1 ml acetic acid and chromium dichloride (1.12 g, 9.15 mmol) were added therein. The mixture was stirred and reacted under the monitor of TLC until no raw material is remained. The solvent was removed by distillation in vacuo. To the residue was added 100 ml water, and extracted by ethyl acetate three times. The organic layer was washed with water, dried, and filtered. The filtrate was subjected rotary evaporation to dryness, and purified via column chromatography, to obtain 555 mg of an off-white solid (i.e., Intermediate 9). ESI(+) m/z: 428.32; 472.31.

Step 5: Preparation of Intermediate 10

To Intermediate 9 mentioned above (450 mg, 1.04 mmol) was added 20 ml of 2M ammonia-methanol solution. The mixture was stirred at room temperature and reacted under the monitor of TLC until no raw material is remained. The reaction mixture was poured into water. The precipitate was purified via column chromatography, to obtain 360 mg of a white solid (i.e., Intermediate 10). ESI(+) m/z: 386.29; 430.29; 486.03.

Step 6: Preparation of Compound 385

Intermediate 10 mentioned above (180 mg, 0.37 mmol) was dissolved in 3 ml dichlormethane, and 0.5 ml trifluoroacetic acid was added therein. The mixture was stirred at room temperature and reacted under the monitor of TLC until no raw material is remained. The reaction mixture was subjected to rotary evaporation to dryness, and dichlormethane was added to the residue. The pH was adjusted to 10 by adding aqueous ammonia. The mixture was separated, and the organic layer was washed with water and dried. The filtrate was subjected to rotary evaporation to dryness, to obtain 150 mg of the title compound as a white solid.

ESI(+) m/z: 386.29.

$^1$H-NMR (CDCl$_3$, 500M): δ (ppm): 6.71 (1H, s, =CH), 4.42-4.68 (2H, m, CH$_2$OH), 2.46 (3H, s, CH$_3$NH), 2.27-2.30 (1H, m), 2.20-2.26 (1H, m), 1.98-2.15 (4H, m), 1.63-1.88 (4H, m), 1.50-1.58 (1H, m), 1.35-1.45 (3H, m), 1.19 (3H, s, CH$_3$), 1.12 (3H, s, CH$_3$), 1.05-1.19 (2H, m), 0.96 (3H, s, CH$_3$), 0.94 (3H, s, CH$_3$), 0.78-0.88 (1H, m), 0.66 (1H, d), 0.41 (1H, d);

$^{13}$C-NMR (CDCl$_3$, 500M): δ (ppm): 196.54, 146.69, 136.09, 68.23, 65.49, 49.31, 45.93, 44.44, 40.48, 34.48, 31.92, 27.35, 26.14, 26.01, 25.83, 25.40, 24.18, 21.84, 20.19, 17.71.

Example 9

(3β,5α)-4,4,14-trimethyl-21-acetoxy-3-(methylamino)-9,19-cyclopregnan-16-en-20-one (Compound 427)

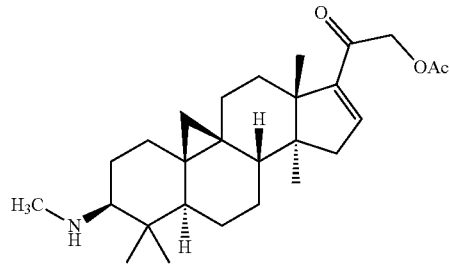

The product in step 4 of Example 8 (Intermediate 9, 100 mg, 0.19 mmol) was dissolved in 5 ml dichlormethane, and 1 ml trifluoroacetic acid was added therein. The mixture was stirred at room temperature and reacted under the monitor of TLC until no raw material is remained. The reaction mixture was subjected to rotary evaporation in vacuo to dryness, and dichlormethane was added to the residue. The pH was adjusted to 8 by adding saturated aqueous sodium bicarbonate. The mixture was separated, and the organic layer was washed with water, dried, and filtered. The filtrate was subjected to rotary evaporation to dryness, to obtain 90 mg of the title compound as a white solid. ESI(+) m/z: 428.30.

$^1$H-NMR (CDCl$_3$, 500M): δ (ppm): 6.83 (1H, s, =CH), 4.86-4.98 (2H, m, CH$_2$OAc), 2.47 (3H, s, CH$_3$NH), 2.43-2.47 (1H, m), 2.21-2.27 (1H, m), 1.99-2.16 (4H, m), 1.64-1.88 (4H, m), 1.52-1.58 (1H, m), 1.36-1.45 (3H, m), 1.19 (3H, s, CH$_3$), 1.12 (3H, s, CH$_3$), 1.05-1.19 (2H, m), 0.96 (3H, s, CH$_3$), 0.94 (3H, s, CH$_3$), 0.78-0.88 (1H, m), 0.66 (1H, d), 0.45 (1H, d).

Example 10

(3β,5α)-4,4,14-trimethyl-3-(methylamino)-21-(3-carboxypropionyloxy)-9,19-cyclopregnan-16-en-20-one hydrochloride (Compound 522)

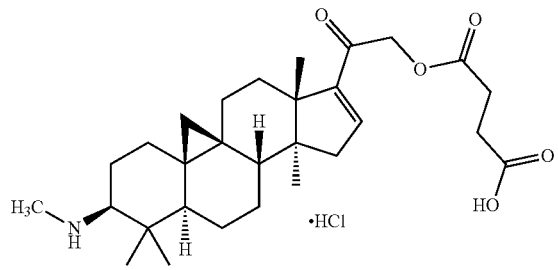

The product in step 5 of Example 8 (Intermediate 10, 100 mg, 0.21 mmol) was dissolved in 2 ml dichlormethane, and 25 mg succinic anhydride and 30 mg pyridine were added therein. The mixture was stirred at room temperature and reacted under the monitor of TLC until no raw material is remained. The reaction mixture was diluted with 10 ml dichlormethane, washed with water, washed with 1% aqueous citric acid, washed with saline, dried, and filtered. The filtrate was concentrated to dryness. The resultant residue was dissolved in 2 ml ethyl acetate, and 0.5 ml of 2M hydrogen chloride-ethyl acetate solution was added therein. The mixture was stirred at room temperature until no raw material is remained, and filtered. The filter cake was washed with a small amount of ethyl acetate, and dried in vacuo to give the title compound as a solid, weighting 75 mg. ESI(+) m/z: 486.40.

$^1$H-NMR (CDCl$_3$, 500M): δ (ppm): 6.72 (1H, s, =CH), 4.72-4.78 (2H, m, CH$_2$O), 2.65-2.68 (2H, m, CH$_2$COOH), 2.52-2.58 (2H, m, CH$_2$CO), 2.50 (3H, s, CH$_3$NH), 2.43-2.47 (1H, m), 2.21-2.27 (1H, m), 1.99-2.16 (4H, m), 1.64-1.88 (4H, m), 1.52-1.58 (1H, m), 1.36-1.45 (3H, m), 1.19 (3H, s, CH$_3$), 1.12 (3H, s, CH$_3$), 1.05-1.19 (2H, m), 0.96 (3H, s, CH$_3$), 0.94 (3H, s, CH$_3$), 0.78-0.88 (1H, m), 0.62 (1H, d), 0.48 (1H, d).

Example 11

(3β,5α)-4,4,14-trimethyl-3-(methylamino)-21-(2-carboxybenzoyloxy)-9,19-cyclopregnan-16-en-20-one hydrochloride (Compound 570)

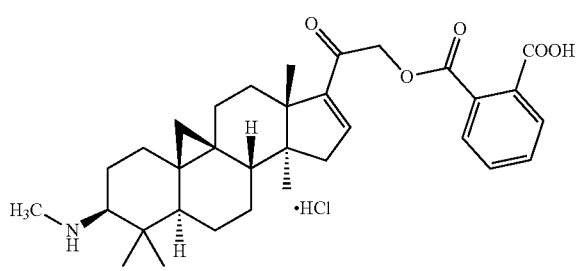

Identical to the process in Example 10, succinic anhydride (25 mg) was replaced by phthalic anhydride (37 mg), to give 80 mg of the title compound. ESI(+) m/z: 534.40.

$^1$H-NMR (CDCl$_3$, 500M): δ (ppm): 8.24 (1H, s), 8.18 (1H, s), 7.72 (1H, s), 7.68 (1H, s), 7.46 (1H, s), 6.78 (1H, s, =CH), 5.76-5.90 (2H, m, CH$_2$O), 2.58 (3H, s, CH$_3$NH), 2.46-2.49 (1H, m), 2.25-2.32 (1H, m), 1.98-2.12 (4H, m), 1.66-1.90 (4H, m), 1.50-1.58 (1H, m), 1.35-1.46 (3H, m), 1.28 (3H, s, CH$_3$), 1.21 (3H, s, CH$_3$), 1.05-1.15 (2H, m), 0.96 (3H, s, CH$_3$), 0.94 (3H, s, CH$_3$), 0.79-0.88 (1H, m), 0.66 (1H, d), 0.58 (1H, d).

Example 12

(3β,5α)-4,4,14-trimethyl-3-(methylamino)-21-(benzoyloxy)-9,19-cyclopregnan-16-en-20-one (Compound 489)

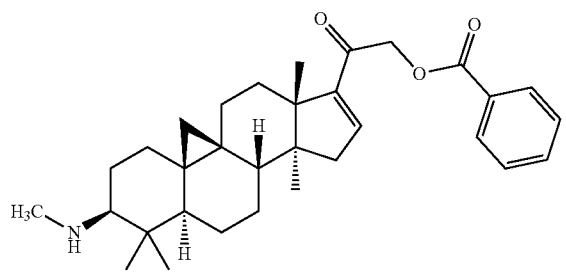

The product in step 5 of Example 8 (Intermediate 10, 95 mg, 0.20 mmol) was dissolved in 2 ml dichlormethane, and 60 mg benzoic anhydride and 30 mg pyridine were added therein. The mixture was stirred at room temperature and reacted under the monitor of TLC until no raw material is remained. The reaction mixture was diluted with 10 ml dichlormethane, washed with water, washed with 1% aqueous citric acid, washed with saline, dried, and filtered. The filtrate was concentrated to dryness. The resultant residue was dissolved in 2 ml dichlormethane, and 0.5 ml trifluoroacetic acid was added therein. The mixture was stirred at room temperature until no raw material is remained. The dichlormethane and trifluoroacetic acid were removed by distillation in vacuo, and dichlormethane was added to the residue. The pH was adjusted to 8 by adding saturated aqueous sodium bicarbonate. The mixture was separated, and the organic layer was washed with water, dried, and filtered. The filtrate was subjected to rotary evaporation to dryness, to obtain 80 mg of the title compound as a white solid. ESI(+) m/z: 486.40.

$^1$H-NMR (CDCl$_3$, 500M): δ (ppm): 8.01 (1H, s), 7.98 (1H, s), 7.52 (1H, s), 7.47 (1H, s), 7.43 (1H, s), 6.56 (1H, s, =CH), 5.76-5.90 (2H, m, CH$_2$O), 2.58 (3H, s, CH$_3$NH), 2.46-2.49 (1H, m), 2.26-2.30 (1H, m), 1.97-2.11 (4H, m), 1.65-1.90 (4H, m), 1.51-1.59 (1H, m), 1.35-1.46 (3H, m), 1.29 (3H, s, CH$_3$), 1.22 (3H, s, CH$_3$), 1.03-1.13 (2H, m), 0.96 (3H, s, CH$_3$), 0.94 (3H, s, CH$_3$), 0.78-0.87 (1H, m), 0.65 (1H, d), 0.56 (1H, d).

Example 13

(3β,5α)-4,4,14-trimethyl-3-(methylamino)-21-methoxy-9,19-cyclopregnan-16-en-20-one (Compound 399)

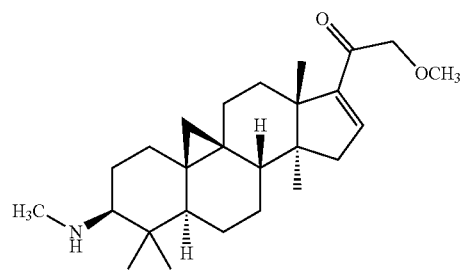

The product in step 5 of Example 8 (Intermediate 10, 100 mg, 0.21 mmol) was dissolved in 2 ml acetone, and a powder potassium carbonate (90 mg, 0.65 mmol) and iodomethane (0.5 ml) were added therein. The mixture was heated to reflux, and reacted under the monitor of TLC until no raw material is remained. The solvent was removed by distillation in vacuo, and the residue was dissolved by 10 ml dichlormethane and water. The mixture was separated, washed with saline, dried, and filtered. The filtrate was concentrated to dryness. The resultant residue was dissolved in 2 ml dichlormethane, and 0.5 ml trifluoroacetic acid was added therein. The mixture was stirred at room temperature until no raw material is remained. The dichlormethane and trifluoroacetic acid were removed by distillation in vacuo, and dichlormethane was added to the residue. The pH was adjusted to 9 by adding conc. aqueous ammonia. The mixture was separated, and the organic layer was washed with water, dried, and filtered. The filtrate was subjected to rotary evaporation to dryness, to obtain 64 mg of the title compound as a white solid. ESI(+) m/z: 400.38.

$^1$H-NMR (CDCl$_3$, 500M): δ (ppm): 6.74 (1H, s, =CH), 4.32-4.45 (2H, m, CH$_2$OH), 3.42 (3H, s, OCH$_3$), 2.59 (3H, s, CH$_3$NH), 2.46-2.52 (1H, m), 2.32-2.36 (1H, m), 2.18-2.25 (4H, m), 1.73-1.89 (4H, m), 1.60-1.68 (1H, m), 1.38-1.46 (3H, m), 1.29 (3H, s, CH$_3$), 1.18 (3H, s, CH$_3$), 1.05-1.13 (2H, m), 0.95 (3H, s, CH$_3$), 0.93 (3H, s, CH$_3$), 0.78-0.88 (1H, m), 0.67 (1H, d), 0.48 (1H, d).

Example 14

(3β,5α)-4,4,14-trimethyl-3-(dimethylamino)-9,19-cyclopregnan-16-en-20-one (Compound 383)

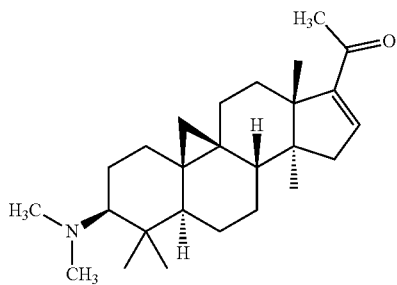

The title compound of Example 1 (100 mg, 0.27 mmol) was dissolved in 4 ml tetrahydrofuran, and 2 ml anhydrous formic acid and 200 mg paraformaldehyde were added therein. The mixture was heated and refluxed to react under the monitor of TLC until no raw material is remained. The mixture was subjected to rotary evaporation to dryness, and dichlormethane was added therein for dissolution. The pH was adjusted to 9 by conc. aqueous ammonia. The mixture was separated and dried. The filtrate was purified via column chromatography using dichlormethane-methanol, to obtain 87 mg of the title compound as a light yellow solid. ESI(+) m/z: 384.27.

$^1$H-NMR (CDCl$_3$, 500M): δ (ppm): 6.65 (1H, s, =CH), 2.42 (6H, s, CH$_3$N), 2.36-2.39 (1H, m), 2.29 (3H, s, CH$_3$CO), 2.20-2.27 (1H, m), 1.97-2.14 (4H, m), 1.62-1.87 (4H, m), 1.50-1.58 (1H, m), 1.38-1.45 (3H, m), 1.21 (3H, s, CH$_3$), 1.15 (3H, s, CH$_3$), 1.05-1.09 (2H, m), 0.96 (3H, s, CH$_3$), 0.94 (3H, s, CH$_3$), 0.78-0.88 (1H, m), 0.66 (1H, d), 0.52 (1H, d).

Example 15

(3β,5α)-4,4,14-trimethyl-3-(dimethylamino)-9,19-cyclopregnan-16-en-20-one oxime (Compound 398a)

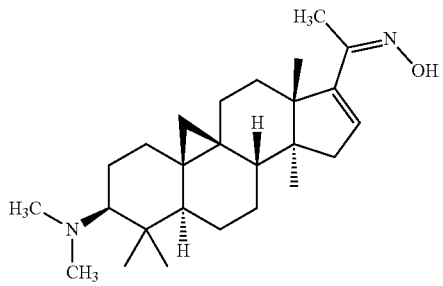

Identical to the preparation process in Example 14, the title compound of Example 1 was replaced by the title compound of Example 2 (100 mg, 0.26 mmol), to give 90 mg of the title compound as a light yellow solid. ESI(+) m/z: 399.30.

$^1$H-NMR (CDCl$_3$, 500M): δ (ppm): 5.82 (1H, s, =CH), 2.36 (6H, s, CH$_3$N), 2.25-2.28 (1H, m), 2.12-2.17 (1H, m), 2.08 (3H, s, CH$_3$CNOH), 1.95-2.01 (4H, m), 1.68-1.90 (4H, m), 1.50-1.58 (1H, m), 1.38-1.48 (3H, m), 1.29 (3H, s, CH$_3$), 1.20 (3H, s, CH$_3$), 1.05-1.15 (2H, m), 0.96 (3H, s, CH$_3$), 0.94 (3H, s, CH$_3$), 0.78-0.88 (1H, m), 0.67 (1H, d), 0.58 (1H, d).

Example 16

(3β,5α)-4,4,14-trimethyl-3-(methylethylamino)-9,19-cyclopregnan-16-en-20-one (Compound 397)

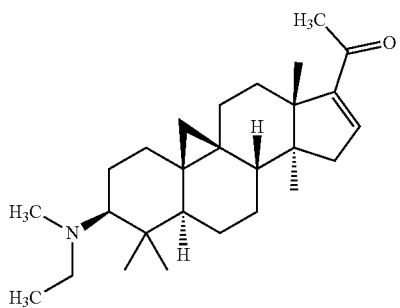

Identical to the preparation process in Example 14, paraformaldehyde was replaced by acetaldehyde (0.5 ml), to give 90 mg of the title compound as an off-white solid. ESI(+) m/z: 398.41.

$^1$H-NMR (CDCl$_3$, 500M): δ (ppm): 6.59 (1H, s, =CH), 2.45 (3H, s, CH$_3$N), 2.36-2.39 (1H, m), 2.29 (3H, s, CH$_3$CO), 2.22-2.28 (2H, m, CH$_2$N), 2.18-2.22 (1H, m), 1.97-2.12 (4H, m), 1.62-1.87 (4H, m), 1.50-1.58 (1H, m), 1.38-1.45 (3H, m), 1.21-1.29 (3H, t, CH$_3$), 1.15 (3H, s, CH$_3$), 1.12 (3H, s, CH$_3$), 1.05-1.09 (2H, m), 0.96 (3H, s, CH$_3$), 0.94 (3H, s, CH$_3$), 0.78-0.88 (1H, m), 0.67 (1H, d), 0.42 (1H, d).

Example 17

(3β,5α)-4,4,14-trimethyl-21-hydroxy-3-(dimethylamino)-9,19-cyclopregnan-16-en-20-one (Compound 399a)

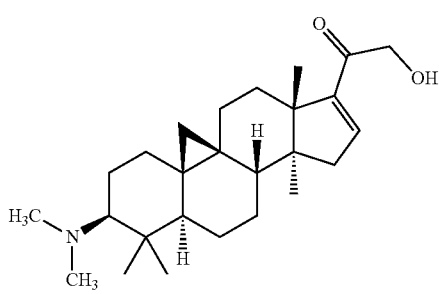

Identical to the preparation process in Example 14, the title compound of Example 1 was replaced by the title compound of Example 8 (100 mg, 0.26 mmol), to give 75 mg of the title compound as a creamy white solid. ESI(+) m/z: 400.39.

$^1$H-NMR (CDCl$_3$, 500M): δ (ppm): 6.70 (1H, s, =CH), 4.40-4.66 (2H, m, CH$_2$OH), 2.46 (6H, s, CH$_3$N), 2.38-2.42 (1H, m), 2.22-2.28 (1H, m), 1.99-2.18 (4H, m), 1.63-1.88 (4H, m), 1.51-1.59 (1H, m), 1.35-1.45 (3H, m), 1.19 (3H, s, CH$_3$), 1.12 (3H, s, CH$_3$), 1.05-1.19 (2H, m), 0.96 (3H, s, CH$_3$), 0.94 (3H, s, CH$_3$), 0.78-0.88 (1H, m), 0.66 (1H, d), 0.45 (1H, d).

Example 18

(3β,5α)-4,4,14-trimethyl-3-(methylcyclopropylamino)-9,19-cyclopregnan-16-en-20-one (Compound 409)

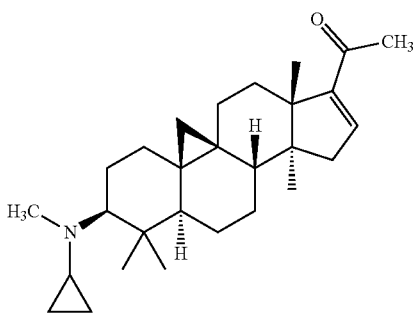

The title compound of Example 1 (500 mg, 1.36 mmol) was dissolved in 10 ml acetone, and powder potassium carbonate (560 mg, 4.06 mmol) and bromocyclopropane (822 mg, 6.8 mol) were added therein. The mixture was heated to reflux, and reacted under the monitor of TLC until no raw material is remained. To the reaction mixture was added dichlormethane and water, and the mixture was separated. The organic layer was washed with water, and dried over anhydrous magnesium sulfate. The filtrate was subjected to rotary evaporation to dryness, to obtain 480 mg of the title compound. ESI(+) m/z: 410.27.

$^1$H-NMR (CDCl$_3$, 500M): δ (ppm): 6.62 (1H, s, =CH), 2.41 (3H, s, CH$_3$NH), 2.36-2.39 (1H, m), 2.28 (3H, s, CH$_3$CO), 2.20-2.26 (1H, m), 1.98-2.15 (4H, m), 1.63-1.88 (4H, m), 1.50-1.58 (1H, m), 1.35-1.45 (3H, m), 1.32 (1H, t, CHN), 1.21 (3H, s, CH$_3$), 1.15 (3H, s, CH$_3$), 1.05-1.19 (2H, m), 0.98 (3H, s, CH$_3$), 0.94 (3H, s, CH$_3$), 0.78-0.88 (1H, m), 0.66 (1H, d), 0.44 (1H, d); 0.40 (2H, m), 0.28 (2H, m).

Example 19

(3β,5α)-4,4,14-trimethyl-16-fluoro-3-(methylamino)-9,19-cyclopregnan-16-en-20-one (Compound 387)

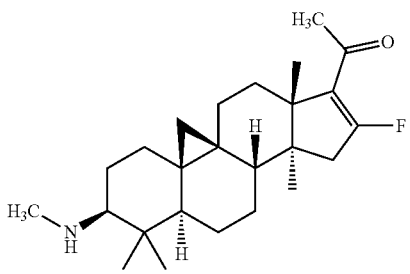

The product in step 1 of Example 8 (Intermediate 6, 200 mg, 0.41 mmol) was suspended in 3 ml of 70% hydrogen fluoride-pyridine solution under the protection of argon, and the mixture was stirred overnight at room temperature. The pH was adjusted to 9 by adding saturated aqueous sodium bicarbonate. The mixture was extracted by dichlormethane, and purified via column chromatography using dichlormethane-methanol, to obtain 48 mg of a white solid, named (3β,5α)-4,4,14-trimethyl-16-fluoro-17-hydroxy-3-(methylamino)-9,19-cyclopregnan-20-one, which was directly used for the next step. ESI(+) m/z: 406.30.

The product mentioned above (48 mg, 0.1 mmol) was suspended in 4 ml toluene, and 0.5 ml concentrated sulfuric acid was added therein. The mixture was heated and refluxed, and reacted under the monitor of TLC until no raw material is remained. The dichlormethane was added therein. The pH was adjusted to 9 by conc. aqueous ammonia, and the mixture was separated. The organic layer was purified via column chromatography using dichlormethane-methanol, to obtain 30 mg of the title compound as a off-white solid. ESI(+) m/z: 388.29.

$^1$H-NMR (CDCl$_3$, 500M): δ (ppm): 2.58 (3H, s, CH$_3$NH), 2.46-2.49 (1H, m), 2.30 (3H, s, CH$_3$CO), 2.22-2.28 (1H, m), 1.98-2.15 (4H, m), 1.63-1.88 (4H, m), 1.50-1.58 (1H, m), 1.35-1.46 (3H, m), 1.20 (3H, s, CH$_3$), 1.13 (3H, s, CH$_3$), 1.05-1.19 (2H, m), 0.95 (3H, s, CH$_3$), 0.93 (3H, s, CH$_3$), 0.78-0.88 (1H, m), 0.67 (1H, d), 0.45 (1H, d).

Example 20

(3β,5α)-4,4,14,16-tetramethyl-3-(methylamino)-9,19-cyclopregnan-16-en-20-one (Compound 383a)

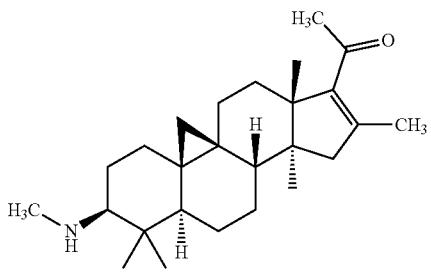

The product in step 1 of Example 8 (Intermediate 6, 1 g, 2.06 mol) was dissolved in 8 ml anhydrous tetrahydrofuran, and a 3M methylmagnesium chloride-tetrahydrofuran solution (0.75 ml) was added slowly therein. The mixture was stirred at room temperature and reacted under the monitor of TLC until no raw material is remained. The pH was adjusted to 6 by adding 1M aqueous hydrochloric acid, and 10 ml ethyl acetate was added therein. The mixture was separated, and the organic layer was subjected to rotary evaporation to dryness, and purified via column chromatography using ethyl acetate-petroleum ether, to obtain 550 mg of a product, named (3β,5α)-4,4,14, 16-tetramethyl-17-hydroxy-3-(methylamino)-9,19-cyclopregnan-20-one. It was directly used for the next step. ESI(+) m/z: 402.32; 446.32; 502.01.

The product mentioned above (550 mg, 1.10 mmol) was dissolved in 20 ml toluene, and 4 ml of concentrated sulfuric acid was added dropwise therein. The mixture was heated and refluxed for 8 h, then cooled to room temperature. The pH was adjusted to 9 by adding saturated aqueous sodium bicarbonate, and the mixture was separated. The organic layer was purified via column chromatography using dichlormethane-methanol, to obtain 200 mg of the title compound as a white solid. ESI(+) m/z: 384.29.

$^1$H-NMR (CDCl$_3$, 500M): δ (ppm): 2.52 (3H, s, CH$_3$NH), 2.42-2.47 (1H, m), 2.32 (3H, s, CH$_3$CO), 2.22-2.28 (1H, m), 1.98-2.15 (4H, m), 1.92 (3H, s) 1.63-1.88 (4H, m), 1.50-1.58 (1H, m), 1.35-1.46 (3H, m), 1.20 (3H, s, CH$_3$), 1.13 (3H, s, CH$_3$), 1.05-1.19 (2H, m), 0.96 (3H, s, CH$_3$), 0.93 (3H, s, CH$_3$), 0.78-0.88 (1H, m), 0.66 (1H, d), 0.42 (1H, d).

Pharmacodynamic Tests and Results a. Effect of the Compound on the Action Potential of the Ventricular Papillary Muscle Cell of Guinea Pig Method: One guinea pig was taken to violently hit the back of the brain such that it fainted. The common carotid artery was cut off for bleeding to kill the guinea pig. The chest was incised to expose the heart, and the ventricle was cut open along the interventricular septum to expose the lumen of the left ventricle. The papillary muscles were quickly taken out and placed in a Kreb's solution saturated with O$_2$ (mixed gas of 95% O$_2$ and 5% CO$_2$) at 0° C. After the microscopic dressing, the papillary muscle specimen was fixed with a stainless steel needle on the silicone rubber at the bottom of the perfusion bath, and perfused with the oxygen-saturated Kreb's solution. The relevant parameters for perfusion: the temperature was 37±0.5° C., and the flow rate was 4 mL/min.

Cellular action potentials were recorded using a conventional electrophysiological method. The glass electrode filled with 3M KCl saturated solution and having a tip resistance of 15-30 MΩ was fixed on the microelectrode manipulator MP-2. The glass electrode was gently inserted into the superficial layer of the prepared papillary muscle specimen using a microelectrode pusher. The electrode was adjusted to provide the predetermined bioelectrical stimulation with the triple-channel SEN-7203 electronic stimulator and SS-202 J isolator. The bioelectrical signal was amplified by the MEZ-8301 amplifier and then input to the computerized electrophysiological recording and analysis system Powerlab 4/25. Subsequently, the relevant parameters of the action potential for the ventricular papillary muscle were analyzed through the analysis system. The relevant parameters for electrical stimulation: 30 ms latency, 7 ms wavewidth, 1 Hz frequency, 52.1 my stimulation intensity.

In the compound screening test stage, after the ventricular papillary muscle specimen of the guinea pig was fixed, it was first perfused with a normal Kreb's solution for about 85 minutes for stabilization, and the relevant parameters of the cellular action potential before administration were recorded at about 80 min after the start of perfusion. The three-limb tube was used to convert the perfusates containing the title compounds. The title compounds were continuously perfused for about 25 min successively with low (0.0005 μM), medium (0.005 μM), and high (0.05 μM) concentrations, respectively. At about 20 min after the start of drug perfusions at different concentrations, the relevant parameters of the action potentials for the ventricular papillary muscle of guinea pig were observed and recorded, respectively. The normal Kreb's solution was used to perfuse and elute for about 25 min during the intervals between drug perfusions at different concentrations.

Further studies based on the expansion of the sample size were carried out for Compound 369, which showed a relatively significant effect on the action potential of the ventricular papillary muscle of guinea pig as indicated in the screening results. The experiment was divided into the following five groups with 6 animals in each group: a vehicle control group, a 369 low dose (0.0005 μM) group, a 369 medium dose (0.005 μM) group, a 369 high dose (0.05 μM) group, and an amiodarone (10 μM) positive control group. After the ventricular papillary muscle specimen of the guinea pig was fixed, it was first perfused with a normal Kreb's solution for about 85 minutes for stabilization, and the relevant parameters of the cellular action potential before administration were recorded at about 80 min after the start of perfusion. According to groups, the three-limb tube was configured to convert the perfusates containing the vehicle, positive control, or Compound 369 at the corresponding concentrations to continuously perfuse for about 25 min. At about 20 min after the start of the perfusions, the relevant parameters of the action potentials for the ventricular papillary muscle of guinea pig were observed and recorded.

FIG. 2 is a typical diagram of action potential. The study results are shown in Table 3 and Table 4. The results in Table 3 indicate that all the title compounds of Examples 1, 3, 8, 9, 10, 11, 14, 17, 19, and 20 have a certain degree of prolonged effects on the APD value of the action potential of the papillary muscle of guinea pig, wherein Compound 369 shows the strongest effect.

The results in Table 4 show that Compound 369 can prolong APD, APD50 and APD90 of the cellular action potential of the ventricular papillary muscle of guinea pig at the concentrations of 0.0005 μM, 0.005 μM and 0.05 μM. The changes are concentration-dependent. The effect of the perfusion at the high concentration of 0.05 μM for 20 min is similar to 10 μM amiodarone, and has a potential antiarrhythmic effect. In the literature, 0.024 μM cyclovirobuxine D can prolong the APD of the action potential of the ventricular myocytes of guinea pig, but 0.012-0.036 μM cyclovirobuxine D makes the spontaneous activity frequency of cardiomyocytes slow down or even disappear. Compound 369 is more sensitive than cyclovirobuxine D, and the dose-effect relationship is definite.

TABLE 3

Effects of the title compounds in the examples on the APD of the cellular action potential of the ventricular papillary muscle of guinea pig

| Group | Time | APD 0.0005 μM | 0.005 μM | 0.05 μM |
| --- | --- | --- | --- | --- |
| Compound 369 (Example 1) | Pre-administration | 0.0719 | 0.0697 | 0.0705 |
| | Post-administration | 0.0912 | 0.1031 | 0.1168 |
| | Change rate (%) | 26.84% | 47.92% | 65.67% |
| Compound 384 (Example 3) | Pre-administration | 0.0734 | 0.0713 | 0.0741 |
| | Post-administration | 0.0890 | 0.0988 | 0.1047 |
| | Change rate (%) | 21.25% | 38.57% | 41.30% |
| Compound 398 (Example 4) | Pre-administration | 0.0701 | 0.0723 | 0.0698 |
| | Post-administration | 0.0695 | 0.771 | 0.764 |
| | Change rate (%) | −0.86% | 6.63% | 9.46% |
| Compound 385 (Example 8) | Pre-administration | 0.0684 | 0.0701 | 0.0696 |
| | Post-administration | 0.0796 | 0.0893 | 0.975 |
| | Change rate (%) | 16.37% | 27.40% | 40.09% |
| Compound 427 (Example 9) | Pre-administration | 0.0764 | 0.0770 | 0.0751 |
| | Post-administration | 0.0903 | 0.0929 | 0.1073 |
| | Change rate (%) | 18.19% | 20.65% | 42.88% |
| Compound 522 (Example 10) | Pre-administration | 0.0801 | 0.0783 | 0.0810 |
| | Post-administration | 0.0824 | 0.0996 | 0.1102 |
| | Change rate (%) | 2.87% | 27.20% | 36.05% |
| Compound 570 (Example 11) | Pre-administration | 0.0724 | 0.0698 | 0.0711 |
| | Post-administration | 0.0813 | 0.0850 | 0.928 |
| | Change rate (%) | 12.29% | 21.78% | 30.52% |
| Compound 489 (Example 12) | Pre-administration | 0.0766 | 0.0757 | 0.0748 |
| | Post-administration | 0.0750 | 0.0771 | 0.820 |
| | Change rate (%) | −2.09% | 1.85% | 9.63% |
| Compound 383 (Example 14) | Pre-administration | 0.0811 | 0.0794 | |
| | Post-administration | 0.0943 | 0.1024 | |
| | Change rate (%) | 16.28% | 28.98% | |
| Compound 397 (Example 16) | Pre-administration | 0.0729 | 0.0733 | 0.0752 |
| | Post-administration | 0.0785 | 0.0711 | 0.0841 |
| | Change rate (%) | 7.68% | −3.00% | 11.84% |
| Compound 399a (Example 17) | Pre-administration | 0.0772 | 0.0786 | 0.0797 |
| | Post-administration | 0.0960 | 0.1010 | 0.1103 |
| | Change rate (%) | 24.35% | 28.50% | 38.39% |
| Compound 409 (Example 18) | Pre-administration | 0.0759 | 0.0738 | 0.0741 |
| | Post-administration | 0.0773 | 0.0762 | 0.0786 |
| | Change rate (%) | 1.84% | 3.25% | 6.07% |
| Compound 387 (Example 19) | Pre-administration | 0.0801 | 0.0788 | 0.0793 |
| | Post-administration | 0.0869 | 0.0944 | 0.0985 |
| | Change rate (%) | 8.49% | 19.80% | 24.21% |
| Compound 383a (Example 20) | Pre-administration | 0.0722 | 0.0709 | 0.0729 |
| | Post-administration | 0.0751 | 0.0943 | 0.0948 |
| | Change rate (%) | 4.02% | 33.00% | 30.04% |

TABLE 4

Effect of Compound 369 on APD, $APD_{50}$, and $APD_{90}$ of the cellular action potential of the ventricular papillary muscle of guinea pig ($\bar{x} \pm SD$, n = 6)

| Group | Time | APD | $APD_{50}$ | $APD_{90}$ |
| --- | --- | --- | --- | --- |
| Parallel control group | Pre-administration | 0.0852 ± 0.0348 | 0.0479 ± 0.0229 | 0.0701 ± 0.0328 |
| | Post-administration | 0.0875 ± 0.0357 | 0.0489 ± 0.0259 | 0.0725 ± 0.0351 |
| | Change rate (%) | 2.92% ± 4.10% | −0.49% ± 8.91% | 2.43% ± 6.35% |
| Compound 369 0.0005 μM | Pre-administration | 0.0661 ± 0.0222 | 0.0365 ± 0.0183 | 0.0537 ± 0.0235 |
| | Post-administration | 0.0930 ± 0.0246[a] | 0.0572 ± 0.0247[a] | 0.0795 ± 0.0260[a] |
| | Change rate (%) | 43.59% ± 17.49%[b] | 49.41% ± 16.99% | 44.30% ± 17.58%[b] |
| Compound 369 0.005 μM | Pre-administration | 0.0732 ± 0.0289 | 0.0428 ± 0.0244 | 0.0604 ± 0.0243 |
| | Post-administration | 0.1023 ± 0.0365[a] | 0.0610 ± 0.0342[a] | 0.0838 ± 0.0345[a] |
| | Change rate (%) | 43.52% ± 23.32%[b] | 47.25% ± 28.78% | 40.25% ± 24.21%[b] |
| Compound 369 0.05 μM | Pre-administration | 0.0738 ± 0.0124 | 0.0385 ± 0.0090 | 0.0603 ± 0.0103 |
| | Post-administration | 0.1199 ± 0.0235[a] | 0.0764 ± 0.0270[a] | 0.1006 ± 0.0242[a] |
| | Change rate (%) | 66.45% ± 39.89%[b] | 101.63% ± 62.10%[b] | 70.81% ± 46.76%[b] |
| Amiodarone 10 μM | Pre-administration | 0.0667 ± 0.0190 | 0.0313 ± 0.0131 | 0.0524 ± 0.0175 |
| | Post-administration | 0.1028 ± 0.0258[a] | 0.0590 ± 0.0269[a] | 0.0862 ± 0.0275[a] |
| | Change rate (%) | 56.83% ± 22.99%[b] | 93.34% ± 53.59%[b] | 68.91% ± 33.59%[b] |

Note:

[a] For APD, $APD_{50}$, and $APD_{90}$ after administration in each group compared to those before administration, $p < 0.05$;

[b] Compared to the parallel control group, for the change rates of APD, $APD_{50}$, and $APD_{90}$ in the groups of samples to be test at low, medium, and high doses as well as the positive control group, $p < 0.05$.

b. Experimental Study on Compound 369 Antagonistic Against the Atrial Fibrillation Induced by High- and Low-Potassium Langendorff Perfusion of the Guinea Pig Heart Objective: to investigate the preventive effect of compound 369 on the atrial fibrillation induced by high- and low-potassium Langendorff perfusion of the guinea pig heart, and provide experimental evidence for the clinical development prospect of compound 369 in treating atrial fibrillation.

Method: a total of 24 guinea pigs were divided into 4 groups according to body weight, and were sacrificed. The heart was quickly taken out, and the blood was squeezed in the ice bath perfusion solution. The heart was quickly transferred in the Langendorff perfusion system, and the perfusion at a constant rate was started by turning on the oxygen-saturated perfusate. One end of the electrode was placed at the cardiac apex, and one end was placed at the right atrium (the position of the atrial appendage). The electrocardiogram was recorded on the computer.

After the heart was stabilized, 10 min after the perfusion of high-K perfusate, blank vehicle, 0.1 μM, 1 μM, and 10 μM of Compound 369, 1 μM Amiodarone and Cyclovirobuxine D were simultaneously administrated and the high K perfusion was continued for 20 min, respectively. Then, the high K perfusion was removed to administrate the low-K perfusate, and the electrocardiogram was obtained at the same time to record whether there was atrial fibrillation within 60 min of low-potassium perfusion.

The results are shown in Table 5. Compared to the vehicle group, the number of animals developing atrial fibrillation was significantly decreased for Compound 369 ranging from 0.1 μM to 10 μM, and was dose-dependent. For the perfusion with 1 μM of Compound 369, the incidence of atrial fibrillation for ex vivo heart was significantly lower than the statistic-based cyclovirobuxine D.

TABLE 5

Incidence of atrial fibrillation in different groups

| Group | Sample for testing | Concentration | Number of animals | Number of animals developing atrial fibrillation | Incidence (%) |
|---|---|---|---|---|---|
| 1 | vehicle | 0 | 6 | 6 | 100 |
| 2 | Compound 369 | 0.1 μM | 5 | 4 | 80 |
| 3 | Compound 369 | 1 μM | 6 | 2 | 33 |
| 4 | Compound 369 | 10 μM | 6 | 0 | 0 |
| 5 | Amiodarone | 1 μM | 6 | 1 | 17 |
| 6 | Cyclovirobuxine D | 1 μM | 6 | 5 | 83 | c. Effect of Compound 369 on the Rat in the Myocardial Ischemia Model with Somatic Coronary Artery Ligation and Reperfusion Method: SD rats were anesthetized with pentobarbital, and a cervical midline incision was made to separate and cut off the trachea such that it was connected to a respirator. The skin was cut along the midline of the left clavicle of the rat, and the chest was opened between the left third and fourth ribs to gently squeeze out the heart. The pericardium was opened, the needle was inserted at the left edge of the pulmonary artery cone and 2 mm at the lower edge of the left atrial appendage. The 6-0 non-invasive suture was threaded through the superficial myocardium, with the left anterior descending coronary artery (LAD) located thereon. After stabilization for 5 min, a double-layer plastic cannula was put on, and the cable tie was tighten to complete the myocardial ischemia induced by left coronary artery occlusion. The criterion for myocardial ischemia is the occurrence of myocardial infarction (St-segment ran up or T-wave was shown as high sharp wave) in the electrocardiogram and the presence of local cyanosis in the heart. After 5 min of myocardial ischemia, the inner cannula was withdrawn, that is, the wire knot was released for reperfusion, and the electrocardiogram of reperfusion in the rat was recorded.

The administration was performed at 5 min before the ischemia by coronary artery ligation, and the administration mode was injection administration (sublingually).

The results are shown in Table 6. Compared with the blank vehicle group, the numbers of animals (incidences) with ventricular premature beat, ventricular tachycardia, ventricular fibrillation, and death were lower for Compound 369 ranging from 1 to 30 mg/kg in concentration than those of the vehicle control group, and were in the dose-response relationship.

TABLE 6

Incidences of ventricular tachycardia and lethal atrial fibrillation in different groups

| Group | Sample for testing | Dose | Number of animals n | Ventricular premature beat n (%) | Ventricular tachycardia n (%) | Ventricular fibrillation n (%) | Death n (%) |
|---|---|---|---|---|---|---|---|
| 1 | vehicle | 0 | 13 | 13 (100) | 13 (100) | 10 (77) | 8 (62) |
| 2 | Compound 369 | 30 mg/kg | 6 | 5 (83) | 1 (17) | 0 (0) | 0 (0) |
| 3 | Compound 369 | 10 mg/kg | 7 | 6 (86) | 5 (71) | 1 (14) | 0 (0) |
| 4 | Compound 369 | 1 mg/kg | 8 | 8 (100) | 8 (100) | 5 (63) | 3 (38) |
| 5 | Amiodarone | 3 mg/kg | 8 | 8 (100) | 7 (87) | 3 (38) | 1 (13) |
| 6 | Cyclovirobuxine D | 1 mg/kg | 6 | 6 (100) | 6 (100) | 5 (83) | 3 (50) | d. Pharmacodynamic Effect of Compound 369 on the Rat Model of Heart Failure Induced by Adriamycin 2 mg/kg of adriamycin was injected through tail vein to a SD rat for modeling, once a week for 6 weeks. After the modeling was completed, intragastrical administration of Compound 369 at low (3 mg/kg) and high (9 mg/kg) doses was carried out daily for 4 weeks. In the negative control group, the same volume of normal saline was injected through the tail vein once a week for 6 weeks, thereafter the same volume of vehicle was intragastrically administered daily for 4 weeks. After the end of the administration, the blood pressure was measured by the carotid artery intubation. The left ventricular end diastolic pressure (LVEDP), left ventricular systolic pressure (LVSP), maximal rate of left ventricular systolic pressure (+dp/dt max), and maximal rate of left ventricular diastolic pressure (−dp/dt max) were recorded, and the average values thereof were calculated.

After the hemodynamic indexes were measured, the chest was opened and the heart and lung were quickly taken out.

They were immediately placed in the normal saline at 4° C. to wash down the remaining blood. The fats, blood vessels and atrial tissues on the heart were discarded. The heart was sucked dry by the filter paper, and accurately weighed using the electronic balance to record the heart weight. The ratio of heart weight to body weight (HW/BW), i.e., the heart mass index (HMI), was calculated.

The results of the cardiac indexes are shown in Table 7. Compared with the negative control group, the heart weights and body weights of the adriamycin-induced model animals were decreased, and the cardiac indexes were increased. Among them, the model control group was the most severe, the low dose group of Compound 369 was the second, and the above indexes in the high-dose group showed the smallest changes. The results of cardiac function indexes are shown in Table 8. Compared to the negative control group, the systolic and diastolic pressures in the model control group and low and high dose groups of Compound 369 were decreased, and the cardiac function indexes such as the left ventricular end diastolic pressure (LVEDP), the left ventricular systolic pressure (LVSP), the maximum rate of left ventricular systolic pressure (+dp/dt max), and the maximum rate of left ventricular diastolic pressure (−dp/dt max) were all impaired to some extent. Among them, the model control group was the most severe, and the low dose and high dose groups of Compound 369 were less impaired than the control group. The above results indicate that Compound 369 has a certain therapeutic effect on heart failure induced by adriamycin.

TABLE 7

Effect of Compound 369 on cardiac indexes of the rat with heart failure induced by adriamycin

| Group | n | BW(g) | HW(mg) | HW/BW(mg) |
|---|---|---|---|---|
| untreated control | 6 | 482.3 ± 27.54 | 1405.4 ± 176.6 | 2.91 |
| Model control | 5 | 235.5 ± 26.16 | 808.4 ± 44.6 | 3.43 |
| Low dose (3 mg/kg) | 6 | 308.5 ± 34.65 | 1007.4 ± 145.3 | 3.27 |
| High dose (9 mg/kg) | 6 | 380.3 ± 24.8 | 1185.0 ± 135.3 | 3.11 |

TABLE 8

Effect of Compound 369 on cardiac function indexes of the model rat with heart failure induced by adriamycin

| Group | n | ASBP (mmHg) | ADBP (mmHg) | LVSP (mmHg) | LVEDP (mmHg) | dp/dtmax (mmHg/s) | −dp/dt max (mmHg/s) |
|---|---|---|---|---|---|---|---|
| Negative control | 6 | 97.3 ± 6.6 | 50.9 ± 19.5 | 104.6 ± 9.7 | −18.4 ± 3.6 | 2684.4 ± 201.3 | −2399.4 ± 289.5 |
| Model control | 5 | 72.5 ± 3.9 | 30.9 ± 6.3 | 85.3 ± 8.9 | −10.5 ± 5.4 | 2116.3 ± 301.8 | −1719.6 ± 315.4 |
| Low dose (3 mg/kg) | 6 | 80.8 ± 17.3 | 40.4 ± 15.3 | 96.5 ± 9.1 | −12.7 ± 10.0 | 2317.7 ± 715.4 | −2013.5 ± 405.4 |
| High dose (9 mg/kg) | 6 | 84.9 ± 13.3 | 47.0 ± 17.1 | 97.3 ± 8.9 | −14.2 ± 8.8 | 2402.3 ± 427.6 | −2098.7 ± 345.9 |

Test for Toxicological Evaluation

The results of the experimental study on the toxicity of Compound 369 administrated through a single intravenous or intragastrical administration in SD rats and KM mice are shown in Table 9.

TABLE 9

MTD values of Compound 369 administrated through a single intravenous or intragastrical administration in SD rats and KM mice

| Compound | Species | Administration mode | Maximum tolerance dose (MTD) |
|---|---|---|---|
| Compound 369 | SD rat | Single intravenous injection | 45 mg/kg |
| Cyclovirobuxine D | SD rat | Single intravenous injection | 5 mg/kg |
| Compound 369 | KM mouse | Single intragastrical administration | 1000 mg/kg |
| Compound 369 | SD rat | Single intragastrical administration | 1000 mg/kg |
| Cyclovirobuxine D | KM mouse | Single intragastrical administration | 400 mg/kg |

The results showed that, the maximum tolerance dose of Compound 369 administrated through the single intravenous injection in the SD rats was 45 mg/kg, which was much higher than 5 mg/kg for cyclovirobuxine D; and the maximum tolerance dose of Compound 369 administrated through the single intragastrical administration in the KM mice was 1000 mg/kg, which was also much higher than 400 mg/kg for cyclovirobuxine D. The above results indicate that Compound 369 is safer than cyclovirobuxine D in rats and mice.

Tests for Pharmacokinetic Evaluation a. Comparative Study on Pharmacokinetics of Cyclovirobuxine D and Compound 369 in SD Rats Method: twelve SD male rats were divided into four groups: 2 mg/kg of Compound 369 or cyclovirobuxine D was single dose through the intravenous injection or intragastrical administration, respectively. In the intravenous and intragastrical groups, blood samples (about 0.3 Ml) were collected from the posterior orbital venous plexus pro-dose and 0.25 h, 0.5 h, 1 h, 2 h, 4 h, 6 h, 8 h, and 12 h post-dose. The concentrations of Compound 369 and cyclovirobuxine D in plasma samples were determined by LC-MS/MS, and the pharmacokinetic parameters were calculated by DAS.3.0 software.

The study results are shown in Table 10. After Compound 369 was administrated to SD rats through the injection and intragastrical administration, the exposures in plasma (AUC and Cmax values) of Compound 369 were slightly lower than that of cyclovirobuxine D, while the half-life ($T_{1/2}$) was significantly shorter than that of cyclovirobuxine D. It can effectively improve the drawbacks in clinical medications, i.e., the serious long-term drug accumulation and the tendency to produce cumulative toxicity due to excessively long half-life.

TABLE 10

Pharmacokinetic parameters in SD rats

| Compound | Dose (mg/kg) | Administration mode | AUCt (ng/mL * h) | $C_{max}$ (ng/mL) | $T_{max}$ (h) | $T_{1/2}$ (h) | F (%) |
|---|---|---|---|---|---|---|---|
| Compound 369 | 2 | Intravenous injection | 249.0 | 103.2 | 0.25 | 4.10 | — |
| Compound 369 | 2 | Intragastrical administration | 84.56 | 11.42 | 5.00 | 3.50 | 35 |
| Cyclovirobuxine D | 2 | Intravenous injection | 310.0 | 146.2 | 0.25 | 8.54 | — |
| Cyclovirobuxine D | 2 | Intragastrical administration | 110.6 | 16.30 | 2.75 | 18.85 | 36 | b. Pharmacokinetic Study in Beagle Canines

Method: Six healthy male Beagle canines were selected and divided into two groups. 2 mg/kg of Compound 369 or cyclovirobuxine D was administrated intragastrically, respectively. Blood samples (about 2 mL) were collected from the limb venous of canines 0 h before administration as well as 0.25 h, 0.5 h, 1 h, 2 h, 4 h, 6 h, 8 h, and 12 h after administration. The concentrations of Compound 369 and cyclovirobuxine D in plasma samples were determined by LC-MS/MS, and the pharmacokinetic parameters were calculated by DAS.3.0 software.

The study results are shown in Table 11. After Compound 369 and cyclovirobuxine D were administrated to canines through the injection and intragastrical administrations, the exposures in plasma (AUC and Cmax values) of Compound 369 were higher than that of cyclovirobuxine D, while the half-life ($T_{1/2}$) was shorter than that of cyclovirobuxine D. It can effectively improve the drawbacks of cyclovirobuxine D in clinical medications, i.e., the obvious long-term drug accumulation and the tendency to produce cumulative toxicity due to excessively long half-life.

TABLE 11

Pharmacokinetic parameters in Beagle canines

| Compound | Dose (mg/kg) | Administration mode | AUCt (ng/mL * h) | $C_{max}$ (ng/mL) | $T_{max}$ (h) | $T_{1/2}$ (h) |
|---|---|---|---|---|---|---|
| Compound 369 | 2 | Intragastrical administration | 505.4 | 43.44 | 2.67 | 11.12 |
| Cyclovirobuxine D | 2 | Intragastrical administration | 274.3 | 19.09 | 3.55 | 15.90 |

Cyclovirobuxine D is a main effective monomer component of Huangyangning. It is mainly clinically used in the treatment of coronary heart disease, arrhythmia, and myocardial ischemia or the like. Due to its long half-life, the long-term medication can produce serious accumulation and prone to produce toxic and side effects, seriously affecting its clinical promotion and application. The above-mentioned results of pharmacokinetic studies on rats and canines showed that the exposure of Compound 369 in rats was slightly lower than that of cyclovirobuxine D, but it was significantly higher in Beagle canines than that of cyclovirobuxine D. It is particularly noteworthy that: whether in rats or in Beagle canines, the metabolic half-life of Compound 369 is significantly shorter than that of cyclovirobuxine D, which is beneficial to improve the drawbacks of cyclovirobuxine D in clinical medications, i.e., the obvious long-term drug accumulation and the tendency to produce cumulative toxicity due to excessively long half-life.

What is claimed is:

1. A compound of general formula (I), an optical isomer thereof or a pharmaceutically acceptable salt thereof:

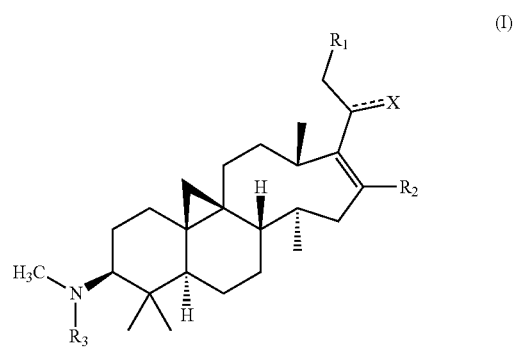

(I)

wherein,
= X represents —OH, =O, =NOR$_a$, or =NOCOR$_b$, wherein R$_a$ represents hydrogen, methyl, ethyl, propyl, isopropyl, or butyl; R$_b$ represents $C_1$-$C_{10}$ alkyl, $C_2$-$C_{10}$ alkenyl, or $C_6$-$C_{12}$ aryl optionally having a substituent, wherein the substituent is selected from halogen, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group;
R$_1$ represents hydrogen, hydroxy, OR$_c$, or OCOR$_d$, wherein R$_c$ represents methyl, ethyl, propyl, isopropyl, butyl, pentyl, cyclopropyl, cyclobutyl, cyclopentyl, or cyclohexyl; R$_d$ represents $C_1$-$C_{10}$ alkyl, $C_3$-$C_{10}$ cycloalkyl, $C_2$-$C_{10}$ alkenyl, $C_6$-$C_{12}$ aryl, or heteroaryl optionally having a substituent, the heteroaryl being a monocyclic or fused ring having 5 to 12 ring atoms and containing 1 to 4 ring heteroatoms selected from N, O, or S, the remaining ring atoms being C; wherein the substituent is selected from halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group;

$R_2$ is selected from hydrogen, halogen, methyl, ethyl, propyl, isopropyl, butyl, pentyl, cyclopropyl, cyclobutyl, cyclopentyl, or cyclohexyl; and $R_3$ is selected from hydrogen, methyl, ethyl, propyl, isopropyl, butyl, pentyl, cyclopropyl, cyclobutyl, cyclopentyl, or cyclohexyl, with a compound wherein $=\!\!=\!X$ represents $=\!\!O$, both $R_1$ and $R_2$ represent H, and $R_3$ represents $CH_3$ being excluded.

2. The compound of formula (I), the optical isomer thereof or the pharmaceutically acceptable salt thereof according to claim 1, wherein:

$=\!\!=\!X$ represents $=\!\!O$ or $=\!\!NOH$;

$R_1$ represents hydrogen, hydroxy, or $OCOR_d$, wherein $R_d$ is $C_1$-$C_{10}$ alkyl, $C_3$-$C_{10}$ cycloalkyl, $C_2$-$C_{10}$ alkenyl, or $C_6$-$C_{12}$ aryl optionally having a substituent; wherein the substituent is selected from halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group;

$R_2$ represents hydrogen, fluorine, or methyl;

$R_3$ represents hydrogen, methyl, ethyl, propyl, isopropyl, or cyclopropyl.

3. The compound of formula (I), the optical isomer thereof or the pharmaceutically acceptable salt thereof according to claim 1, wherein:

$=\!\!=\!X$ represents $=\!\!O$, and $R_2=\!R_3=\!H$;

$R_1$ represents hydrogen, hydroxy, or $OCOR_d$, wherein $R_d$ is $C_1$-$C_{10}$ alkyl, vinyl, or phenyl optionally having a substituent, wherein the substituent is halogen, trifluoromethyl, methyl, ethyl, hydroxy, amino, sulfhydryl, phenyl, methoxy, ethoxy, cyano, nitro, acetoxy, acetylamino, carboxy, a methyl carboxylate group, or an ethyl carboxylate group.

4. The compound of formula (I), the optical isomer thereof or the pharmaceutically acceptable salt thereof according to claim 3, wherein:

$R_1$ represents:

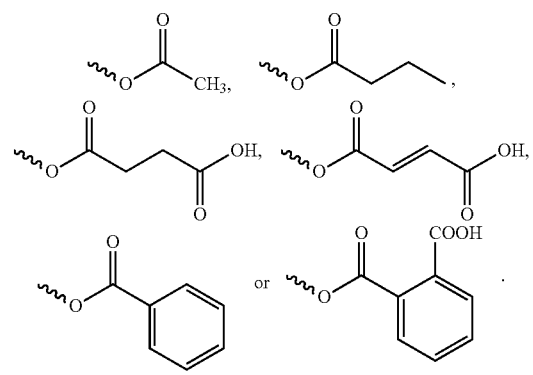

5. The compound of formula (I), the optical isomer thereof or the pharmaceutically acceptable salt thereof according to claim 1, wherein the compound is a compound selected from any one of the following structures:

(3β,5α)-4,4,14-trimethyl-3-(methylamino)-9,19-cyclopregnan-16-en-20-one;

(3β,5α)-4,4,14-trimethyl-3-(methylamino)-9,19-cyclopregnan-16-en-20-one oxime;

(3β,5α)-4,4,14-trimethyl-3-(methylamino)-20-methoxyimino-9,19-cyclopregnan-16-ene;

(3β,5α)-4,4,14-trimethyl-21-hydroxy-3-(methylamino)-9,19-cyclopregnan-16-en-20-one;

(3β,5α)-4,4,14-trimethyl-21-acetoxy-3-(methylamino)-9,19-cyclopregnan-16-en-20-one;

(3β,5α)-4,4,14-trimethyl-3-(methylamino)-21-(3-carboxypropionyloxy)-9,19-cyclopregnan-16-en-20-one hydrochloride;

(3β,5α)-4,4,14-trimethyl-3-(methylamino)-21-(2-carboxybenzoyloxy)-9,19-cyclopregnan-16-en-20-one hydrochloride;

(3β,5α)-4,4,14-trimethyl-3-(methylamino)-21-(benzoyloxy)-9,19-cyclopregnan-16-en-20-one;

(3β,5α)-4,4,14-trimethyl-3-(methylethylamino)-9,19-cyclopregnan-16-en-20-one;

(3β,5α)-4,4,14-trimethyl-21-hydroxy-3-(dimethylamino)-9,19-cyclopregnan-16-en-20-one;

(3β,5α)-4,4,14-trimethyl-3-(methylcyclopropylamino)-9,19-cyclopregnan-16-en-20-one;

(3β,5α)-4,4,14-trimethyl-16-fluoro-3-(methylamino)-9,19-cyclopregnan-16-en-20-one; or (3β,5α)-4,4,14,16-tetramethyl-3-(methylamino)-9,19-cyclopregnan-16-en-20-one.

6. The compound of formula (I), the optical isomer thereof or the pharmaceutically acceptable salt thereof according to claim 1, wherein the pharmaceutically acceptable salt is a salt formed from the compound of formula (I) with an acid selected from hydrochloric acid, hydrobromic acid, methanesulfonic acid, isethionic acid, sulfuric acid, acetic acid, trifluoroacetic acid, maleic acid, benzenesulfonic acid, toluenesulfonic acid, nitric acid, phosphoric acid, boric acid, tartaric acid, citric acid, succinic acid, benzoic acid, ascorbic acid, or salicylic acid.

7. A pharmaceutical composition comprising the compound of formula (I), the optical isomer thereof or the pharmaceutically acceptable salt thereof according to claim 1, and a pharmaceutically acceptable carrier.

8. A pharmaceutical composition comprising the compound of formula (I), the optical isomer thereof or the pharmaceutically acceptable salt thereof according to claim 2, and a pharmaceutically acceptable carrier.

9. A pharmaceutical composition comprising the compound of formula (I), the optical isomer thereof or the pharmaceutically acceptable salt thereof according to claim 3, and a pharmaceutically acceptable carrier.

10. A pharmaceutical composition comprising the compound of formula (I), the optical isomer thereof or the pharmaceutically acceptable salt thereof according to claim 4, and a pharmaceutically acceptable carrier.

11. A pharmaceutical composition comprising the compound of formula (I), the optical isomer thereof or the pharmaceutically acceptable salt thereof according to claim 5, and a pharmaceutically acceptable carrier.

12. A pharmaceutical composition comprising the compound of formula (I), the optical isomer thereof or the pharmaceutically acceptable salt thereof according to claim 6, and a pharmaceutically acceptable carrier.

13. A method of treating a cardiovascular or cerebrovascular disease, comprising administering to a subject in need thereof the compound of formula (I), the optical isomer thereof or the pharmaceutically acceptable salt thereof of claim 1;

wherein the cardiovascular or cerebrovascular disease is arrhythmia, asymptomatic myocardial ischemia, ischemic cardiomyopathy, heart failure, or a complication thereof.

\* \* \* \* \*

UNITED STATES PATENT AND TRADEMARK OFFICE
CERTIFICATE OF CORRECTION

PATENT NO. : 10,568,892 B2  Page 1 of 1
APPLICATION NO. : 16/083390
DATED : February 25, 2020
INVENTOR(S) : Shanchun Zhang et al.

It is certified that error appears in the above-identified patent and that said Letters Patent is hereby corrected as shown below:

On the Title Page

Column 1, Item (87), under "PCT Pub. Date":
Delete "May 30, 2018" and insert -- May 3, 2018 -- therefor.

In the Claims

Column 40, Line 21:
Claim 1, after "of" delete "general".

Column 40, Lines 25-35:

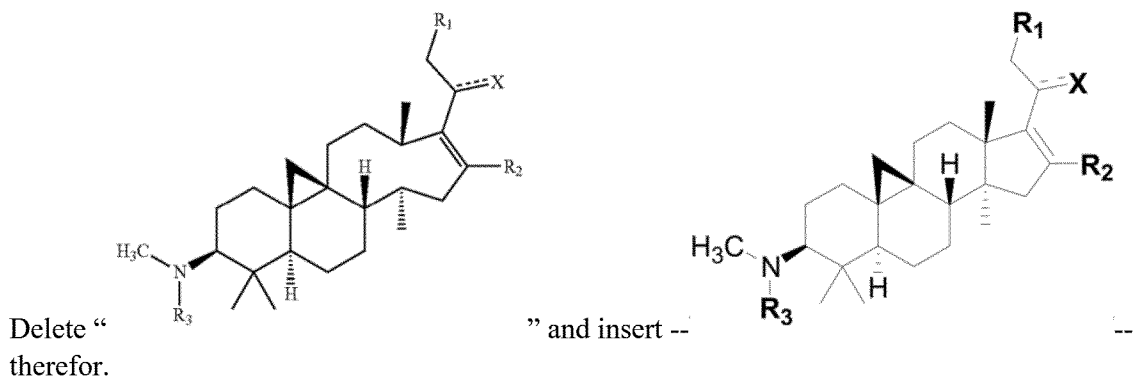

Delete " " and insert -- -- therefor.

Signed and Sealed this
Nineteenth Day of May, 2020

Andrei Iancu
*Director of the United States Patent and Trademark Office*